(12) United States Patent
Lamson et al.

(10) Patent No.: US 10,912,637 B2
(45) Date of Patent: Feb. 9, 2021

(54) DEVICES, SYSTEMS AND METHODS FOR TREATING BENIGN PROSTATIC HYPERPLASIA AND OTHER CONDITIONS

(71) Applicant: NeoTract, Inc., Pleasanton, CA (US)

(72) Inventors: Theodore C. Lamson, Pleasanton, CA (US); Floria Cheng, San Francisco, CA (US); Joseph Catanese, III, San Leandro, CA (US)

(73) Assignee: NeoTract, Inc., Pleasanton, CA (US)

(*) Notice: Subject to any disclaimer, the term of this patent is extended or adjusted under 35 U.S.C. 154(b) by 0 days.

(21) Appl. No.: 16/433,054

(22) Filed: Jun. 6, 2019

(65) Prior Publication Data
US 2019/0365522 A1 Dec. 5, 2019

Related U.S. Application Data

(63) Continuation of application No. 16/234,282, filed on Dec. 27, 2018, which is a continuation of application
(Continued)

(51) Int. Cl.
A61F 2/04 (2013.01)
A61B 17/04 (2006.01)
(Continued)

(52) U.S. Cl.
CPC ............ A61F 2/04 (2013.01); A61B 17/0401 (2013.01); A61B 17/0469 (2013.01); A61B 17/0482 (2013.01); A61B 17/0487 (2013.01); A61B 17/06109 (2013.01); A61B 17/42 (2013.01); A61B 17/00234 (2013.01); A61B 17/0218 (2013.01); A61B 17/0467 (2013.01); A61B 17/3468 (2013.01); A61B 17/3478 (2013.01); A61B 18/14 (2013.01); A61B 18/1815 (2013.01); A61B 18/20 (2013.01); A61B 2017/00022 (2013.01); A61B 2017/00274 (2013.01); A61B 2017/00792 (2013.01);
(Continued)

(58) Field of Classification Search
CPC . A61B 2017/00274; A61B 2018/00547; A61F 2/04
See application file for complete search history.

(56) References Cited

U.S. PATENT DOCUMENTS 659,422 A 10/1900 Shidler
780,392 A 1/1905 Wanamaker et al.
(Continued)

FOREIGN PATENT DOCUMENTS

CA 2477220 11/2007
CN 1697633 A 11/2005
(Continued)

OTHER PUBLICATIONS

Bacharova, O.A., et al. "The Effect of Rhodiolae rosea Extract on Incidence Rate of Superficial Bladder Carcinoma Relapses", Kozin 1995.
(Continued)

Primary Examiner — Gregory A Anderson
(74) Attorney, Agent, or Firm — Christopher J. Buchko

(57) ABSTRACT

Extra-urethral implants and methods of use are disclosed. Implants can treat disorders or diseases of the prostate by, for example, enlarging the lumen of the prostatic urethra.

16 Claims, 12 Drawing Sheets

Related U.S. Application Data

No. 13/830,811, filed on Mar. 14, 2013, now Pat. No. 10,195,014.

(51) Int. Cl.
  *A61B 17/06* (2006.01)
  *A61B 17/42* (2006.01)
  *A61B 18/00* (2006.01)
  *A61B 18/14* (2006.01)
  *A61B 18/18* (2006.01)
  *A61B 18/20* (2006.01)
  *A61B 17/00* (2006.01)
  *A61B 17/02* (2006.01)
  *A61B 17/34* (2006.01)

(52) U.S. Cl.
  CPC .............. *A61B 2017/00796* (2013.01); *A61B 2017/00805* (2013.01); *A61B 2017/0404* (2013.01); *A61B 2017/0409* (2013.01); *A61B 2017/0417* (2013.01); *A61B 2017/0419* (2013.01); *A61B 2017/0451* (2013.01); *A61B 2017/0454* (2013.01); *A61B 2017/0456* (2013.01); *A61B 2017/0458* (2013.01); *A61B 2017/0462* (2013.01); *A61B 2017/0464* (2013.01); *A61B 2017/0488* (2013.01); *A61B 2017/06052* (2013.01); *A61B 2017/06176* (2013.01); *A61B 2018/00547* (2013.01)

(56) References Cited

U.S. PATENT DOCUMENTS

| | | |
|---|---|---|
| 789,467 A | 5/1905 | West |
| 2,360,164 A | 10/1944 | Frank |
| 2,485,531 A | 10/1949 | William et al. |
| 2,579,192 A | 12/1951 | Alexander |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Mckenzie |
| 3,326,586 A | 6/1967 | Frost et al. |
| 3,470,834 A | 10/1969 | Bone |
| 3,521,918 A | 7/1970 | Hammond |
| 3,541,591 A | 11/1970 | Hoegerman |
| 3,664,345 A | 5/1972 | Dabbs et al. |
| 3,713,680 A | 1/1973 | Pagano |
| 3,716,058 A | 2/1973 | Tanner |
| 3,756,638 A | 9/1973 | Stockberger |
| 3,873,140 A | 3/1975 | Bloch |
| 3,875,648 A | 4/1975 | Bone |
| 3,886,933 A | 6/1975 | Mori et al. |
| 3,931,667 A | 1/1976 | Merser et al. |
| 3,976,079 A | 8/1976 | Samuels et al. |
| 4,006,747 A | 2/1977 | Kronenthal et al. |
| 4,137,920 A | 2/1979 | Bonnet |
| 4,164,225 A | 8/1979 | Johnson et al. |
| 4,210,148 A | 7/1980 | Stivala |
| 4,235,238 A | 11/1980 | Ogiu et al. |
| 4,291,698 A | 9/1981 | Fuchs et al. |
| 4,409,974 A | 10/1983 | Freedland |
| 4,419,094 A | 12/1983 | Patel |
| 4,452,236 A | 6/1984 | Utsugi |
| 4,493,323 A | 1/1985 | Albright et al. |
| 4,513,746 A | 4/1985 | Aranyi et al. |
| 4,621,640 A | 11/1986 | Mulhollan et al. |
| 4,655,771 A | 4/1987 | Wallsten |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,863,439 A | 9/1989 | Sanderson |
| 4,893,623 A | 1/1990 | Rosenbluth |
| 4,899,743 A | 2/1990 | Nicholson et al. |
| 4,926,860 A | 5/1990 | Stice et al. |
| 4,935,028 A | 6/1990 | Drews |
| 4,946,468 A | 8/1990 | Li |
| 4,955,859 A | 9/1990 | Zilber |
| 4,955,913 A | 9/1990 | Robinson |
| 4,968,315 A | 11/1990 | Gattuma |
| 4,994,066 A | 2/1991 | Voss |
| 5,002,550 A | 3/1991 | Li |
| 5,019,032 A | 5/1991 | Robertson |
| 5,041,129 A | 8/1991 | Hayhurst et al. |
| 5,046,513 A | 9/1991 | Gattuma et al. |
| 5,053,046 A | 10/1991 | Janese |
| 5,078,731 A | 1/1992 | Hayhurst |
| 5,080,660 A | 1/1992 | Buelna |
| 5,098,374 A | 3/1992 | Othel-Jacobsen et al. |
| 5,100,421 A | 3/1992 | Christoudias |
| 5,123,914 A | 6/1992 | Cope |
| 5,127,393 A | 7/1992 | McFarlin et al. |
| 5,129,912 A | 7/1992 | Noda et al. |
| 5,133,713 A | 7/1992 | Huang et al. |
| 5,159,925 A | 11/1992 | Neuwirth et al. |
| 5,160,339 A | 11/1992 | Chen et al. |
| 5,163,960 A | 11/1992 | Bonutti |
| 5,167,614 A | 12/1992 | Tessmann et al. |
| 5,192,303 A | 3/1993 | Gattuma et al. |
| 5,203,787 A | 4/1993 | Noblitt et al. |
| 5,207,672 A | 5/1993 | Roth et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,237,984 A | 8/1993 | Williams et al. |
| 5,254,126 A | 10/1993 | Filipi et al. |
| 5,258,015 A | 11/1993 | Li et al. |
| 5,267,960 A | 12/1993 | Hayman et al. |
| 5,269,802 A * | 12/1993 | Garber .................. A61B 17/29 604/8 |
| 5,269,809 A | 12/1993 | Hayhurst et al. |
| 5,300,099 A | 4/1994 | Rudie |
| 5,306,280 A | 4/1994 | Bregen et al. |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler et al. |
| 5,350,399 A | 9/1994 | Erlebacher et al. |
| 5,354,271 A | 10/1994 | Voda |
| 5,358,511 A | 10/1994 | Gattuma et al. |
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,370,661 A | 12/1994 | Branch |
| 5,372,600 A | 12/1994 | Beyar et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,409,453 A | 4/1995 | Lundquist et al. |
| 5,411,520 A | 5/1995 | Nash et al. |
| 5,417,691 A | 5/1995 | Hayhurst |
| 5,435,805 A | 7/1995 | Edwards et al. |
| 5,441,485 A | 8/1995 | Peters |
| 5,458,612 A | 10/1995 | Chin |
| 5,464,416 A | 11/1995 | Steckel |
| 5,470,308 A | 11/1995 | Edwards et al. |
| 5,470,337 A | 11/1995 | Moss |
| 5,472,446 A | 12/1995 | Torre |
| 5,480,406 A | 1/1996 | Nolan et al. |
| 5,499,994 A | 3/1996 | Tihon et al. |
| 5,501,690 A | 3/1996 | Measamer et al. |
| 5,507,754 A | 4/1996 | Green et al. |
| 5,522,846 A | 6/1996 | Bonutti |
| 5,531,759 A | 7/1996 | Kensey et al. |
| 5,531,763 A | 7/1996 | Mastri et al. |

(56) References Cited

U.S. PATENT DOCUMENTS

| | | | |
|---|---|---|---|
| 5,534,012 A | 7/1996 | Bonutti | |
| 5,536,240 A | 7/1996 | Edwards et al. | |
| 5,540,655 A | 7/1996 | Edwards et al. | |
| 5,540,701 A * | 7/1996 | Sharkey | A61B 17/11 606/153 |
| 5,540,704 A | 7/1996 | Gordon et al. | |
| 5,542,594 A | 8/1996 | McKean et al. | |
| 5,545,171 A | 8/1996 | Sharkey et al. | |
| 5,545,178 A | 8/1996 | Kensey et al. | |
| 5,549,631 A | 8/1996 | Bonutti | |
| 5,550,172 A | 8/1996 | Regula et al. | |
| 5,554,162 A | 9/1996 | DeLange | |
| 5,554,171 A | 9/1996 | Gattuma et al. | |
| 5,562,688 A | 10/1996 | Riza | |
| 5,562,689 A | 10/1996 | Green et al. | |
| 5,569,305 A | 10/1996 | Bonutti | |
| 5,571,104 A | 11/1996 | Li | |
| 5,573,540 A | 11/1996 | Yoon | |
| 5,578,044 A | 11/1996 | Gordon et al. | |
| 5,591,177 A | 1/1997 | Lehrer | |
| 5,591,179 A | 1/1997 | Edelstein | |
| 5,593,421 A | 1/1997 | Bauer | |
| 5,611,515 A | 3/1997 | Benderev et al. | |
| 5,620,461 A | 4/1997 | Moer et al. | |
| 5,626,614 A | 5/1997 | Hart | |
| 5,630,824 A | 5/1997 | Hart | |
| 5,643,321 A | 7/1997 | McDevitt | |
| 5,647,836 A | 7/1997 | Blake et al. | |
| 5,653,373 A | 8/1997 | Green et al. | |
| 5,665,109 A | 9/1997 | Yoon | |
| 5,667,486 A | 9/1997 | Mikulich et al. | |
| 5,667,488 A | 9/1997 | Lundquist et al. | |
| 5,667,522 A | 9/1997 | Flomenblit et al. | |
| 5,669,917 A | 9/1997 | Sauer et al. | |
| 5,672,171 A | 9/1997 | Andrus et al. | |
| 5,690,649 A | 11/1997 | Li | |
| 5,690,677 A | 11/1997 | Schmieding et al. | |
| 5,697,950 A | 12/1997 | Fucci et al. | |
| 5,707,394 A | 1/1998 | Miller et al. | |
| 5,716,368 A | 2/1998 | Torre et al. | |
| 5,718,717 A | 2/1998 | Bonutti | |
| 5,725,556 A | 3/1998 | Moser et al. | |
| 5,725,557 A | 3/1998 | Gattuma et al. | |
| 5,733,306 A | 3/1998 | Bonutti | |
| 5,741,276 A | 4/1998 | Poloyko et al. | |
| 5,746,753 A | 5/1998 | Sullivan et al. | |
| 5,749,846 A | 5/1998 | Edwards et al. | |
| 5,749,889 A | 5/1998 | Bacich et al. | |
| 5,752,963 A | 5/1998 | Allard et al. | |
| 5,775,328 A | 7/1998 | Lowe et al. | |
| 5,782,862 A | 7/1998 | Bonutti | |
| 5,782,864 A | 7/1998 | Lizardi | |
| 5,791,022 A | 8/1998 | Bohman | |
| 5,800,445 A | 9/1998 | Ratcliff et al. | |
| 5,807,403 A | 9/1998 | Beyar et al. | |
| 5,810,848 A | 9/1998 | Hayhurst | |
| 5,810,853 A | 9/1998 | Yoon | |
| 5,814,072 A | 9/1998 | Bonutti | |
| 5,830,179 A | 11/1998 | Mikus et al. | |
| 5,830,221 A | 11/1998 | Stein et al. | |
| 5,845,645 A | 12/1998 | Bonutti | |
| 5,846,254 A | 12/1998 | Schulze et al. | |
| 5,861,002 A | 1/1999 | Desai | |
| 5,868,762 A | 2/1999 | Cragg et al. | |
| 5,873,891 A | 2/1999 | Sohn | |
| 5,879,357 A | 3/1999 | Heaton et al. | |
| 5,897,574 A | 4/1999 | Bonutti | |
| 5,899,911 A | 5/1999 | Carter | |
| 5,899,921 A | 5/1999 | Caspari et al. | |
| 5,904,679 A | 5/1999 | Clayman | |
| 5,904,696 A | 5/1999 | Rosenman | |
| 5,908,428 A | 6/1999 | Scirica et al. | |
| 5,908,447 A | 6/1999 | Schroeppel et al. | |
| 5,919,198 A | 7/1999 | Graves et al. | |
| 5,919,202 A | 7/1999 | Yoon | |
| 5,921,982 A | 7/1999 | Lesh et al. | |
| 5,921,986 A | 7/1999 | Bonutti | |
| 5,928,252 A | 7/1999 | Steadman et al. | |
| 5,931,844 A | 8/1999 | Thompson et al. | |
| 5,941,439 A | 8/1999 | Kammerer et al. | |
| 5,944,739 A | 8/1999 | Zlock et al. | |
| 5,948,000 A | 9/1999 | Larsen et al. | |
| 5,948,001 A | 9/1999 | Larsen | |
| 5,948,002 A | 9/1999 | Bonutti | |
| 5,954,057 A | 9/1999 | Li | |
| 5,954,747 A | 9/1999 | Clark | |
| 5,964,732 A | 10/1999 | Willard | |
| 5,971,447 A | 10/1999 | Steck | |
| 5,971,967 A | 10/1999 | Willard | |
| 6,010,514 A | 1/2000 | Burney et al. | |
| 6,011,525 A | 1/2000 | Piole | |
| 6,015,428 A | 1/2000 | Pagedas | |
| 6,024,751 A | 2/2000 | Lovato et al. | |
| 6,030,393 A | 2/2000 | Corlew | |
| 6,033,413 A | 3/2000 | Mikus et al. | |
| 6,033,430 A | 3/2000 | Bonutti | |
| 6,036,701 A | 3/2000 | Rosenman | |
| 6,048,351 A | 4/2000 | Gordon et al. | |
| 6,053,908 A | 4/2000 | Crainich et al. | |
| 6,053,935 A | 4/2000 | Brenneman et al. | |
| 6,056,722 A | 5/2000 | Jayaraman | |
| 6,056,772 A | 5/2000 | Bonutti | |
| 6,066,160 A | 5/2000 | Colvin et al. | |
| 6,068,648 A | 5/2000 | Cole et al. | |
| 6,080,167 A | 6/2000 | Lyell | |
| 6,086,608 A | 7/2000 | Ek et al. | |
| 6,110,183 A | 8/2000 | Cope | |
| 6,117,133 A | 9/2000 | Zappala | |
| 6,117,160 A | 9/2000 | Bonutti | |
| 6,117,161 A | 9/2000 | Li et al. | |
| 6,120,539 A | 9/2000 | Eldridge et al. | |
| 6,132,438 A | 10/2000 | Fleischman et al. | |
| 6,139,555 A | 10/2000 | Hart et al. | |
| RE36,974 E | 11/2000 | Bonutti | |
| 6,143,006 A | 11/2000 | Chan | |
| 6,152,935 A | 11/2000 | Kammerer et al. | |
| 6,156,044 A | 12/2000 | Kammerer et al. | |
| 6,156,049 A | 12/2000 | Lovato et al. | |
| 6,159,207 A | 12/2000 | Yoon | |
| 6,159,234 A | 12/2000 | Bonutti et al. | |
| 6,193,714 B1 | 2/2001 | McGaffigan et al. | |
| 6,200,329 B1 | 3/2001 | Fung et al. | |
| 6,203,565 B1 | 3/2001 | Bonutti et al. | |
| 6,206,895 B1 | 3/2001 | Levinson | |
| 6,206,907 B1 | 3/2001 | Marino et al. | |
| 6,228,096 B1 | 5/2001 | Marchand | |
| 6,235,024 B1 | 5/2001 | Tu | |
| 6,258,124 B1 | 7/2001 | Darois et al. | |
| 6,261,302 B1 | 7/2001 | Voegele et al. | |
| 6,261,320 B1 | 7/2001 | Tam et al. | |
| 6,270,530 B1 | 8/2001 | Eldridge et al. | |
| 6,280,441 B1 | 8/2001 | Ryan | |
| 6,280,460 B1 | 8/2001 | Bolduc et al. | |
| 6,287,317 B1 | 9/2001 | Makower et al. | |
| 6,290,711 B1 | 9/2001 | Caspari et al. | |
| 6,306,158 B1 | 10/2001 | Bartlett | |
| 6,312,448 B1 | 11/2001 | Bonutti | |
| 6,319,263 B1 | 11/2001 | Levinson | |
| 6,322,112 B1 | 11/2001 | Duncan | |
| 6,332,889 B1 | 12/2001 | Sancoff et al. | |
| 6,382,214 B1 | 5/2002 | Raz et al. | |
| 6,387,041 B1 | 5/2002 | Harari et al. | |
| 6,398,795 B1 | 6/2002 | McAlister et al. | |
| 6,398,796 B2 | 6/2002 | Levinson | |
| 6,425,900 B1 | 7/2002 | Knodel et al. | |
| 6,425,919 B1 | 7/2002 | Lambrecht | |
| 6,428,538 B1 | 8/2002 | Blewett et al. | |
| 6,428,562 B2 | 8/2002 | Bonutti | |
| 6,436,107 B1 | 8/2002 | Wang et al. | |
| 6,461,355 B2 | 10/2002 | Svejkovsky et al. | |
| 6,482,235 B1 | 11/2002 | Lambrecht et al. | |
| 6,488,691 B1 | 12/2002 | Carroll et al. | |
| 6,491,672 B2 | 12/2002 | Slepian et al. | |
| 6,491,707 B2 | 12/2002 | Makower et al. | |

(56) References Cited

U.S. PATENT DOCUMENTS

| | | |
|---|---|---|
| 6,494,888 B1 | 12/2002 | Laufer et al. |
| 6,500,184 B1 | 12/2002 | Chan et al. |
| 6,500,195 B2 | 12/2002 | Bonutti |
| 6,506,190 B1 | 1/2003 | Walshe |
| 6,506,196 B1 | 1/2003 | Laufer |
| 6,514,247 B1 | 2/2003 | McGaffigan et al. |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,533,796 B1 | 3/2003 | Sauer et al. |
| 6,544,230 B1 | 4/2003 | Flaherty et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,582,453 B1 | 6/2003 | Tran et al. |
| 6,592,609 B1 | 7/2003 | Bonutti |
| 6,595,911 B2 | 7/2003 | LoVuolo |
| 6,596,013 B2 | 7/2003 | Yang et al. |
| 6,599,311 B1 | 7/2003 | Biggs et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | Goar et al. |
| 6,638,275 B1 | 10/2003 | McGaffigan et al. |
| 6,641,524 B2 | 11/2003 | Kovac |
| 6,641,592 B1 | 11/2003 | Sauer et al. |
| 6,656,182 B1 | 12/2003 | Hayhurst |
| 6,660,008 B1 | 12/2003 | Foerster et al. |
| 6,660,023 B2 | 12/2003 | McDevitt et al. |
| 6,663,589 B1 | 12/2003 | Halevy |
| 6,663,633 B1 | 12/2003 | Pierson |
| 6,663,639 B1 | 12/2003 | Laufer et al. |
| 6,699,263 B2 | 3/2004 | Cope |
| 6,702,846 B2 | 3/2004 | Mikus et al. |
| 6,706,047 B2 | 3/2004 | Trout et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,790,223 B2 | 9/2004 | Reever |
| 6,802,838 B2 | 10/2004 | Loeb et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Bolea et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,921,361 B2 | 7/2005 | Suzuki et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,986,784 B1 | 1/2006 | Weiser et al. |
| 6,988,983 B2 | 1/2006 | Connors et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,004,965 B2 | 2/2006 | Gross |
| 7,008,381 B2 | 3/2006 | Janssens |
| 7,011,688 B2 | 3/2006 | Gryska et al. |
| 7,015,253 B2 | 3/2006 | Escandon et al. |
| 7,041,111 B2 | 5/2006 | Chu |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,063,715 B2 | 6/2006 | Onuki et al. |
| 7,065,325 B2 | 6/2006 | Zegelin et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,096,301 B2 | 8/2006 | Beaudoin et al. |
| 7,104,949 B2 | 9/2006 | Anderson et al. |
| 7,105,004 B2 | 9/2006 | DiCesare et al. |
| 7,108,655 B2 | 9/2006 | Whalen et al. |
| 7,112,226 B2 * | 9/2006 | Gellman .................. A61F 2/04 604/8 |
| 7,141,038 B2 | 11/2006 | Whalen et al. |
| 7,153,314 B2 | 12/2006 | Laufer et al. |
| 7,179,225 B2 | 2/2007 | Shluzas et al. |
| 7,226,558 B2 | 6/2007 | Nieman et al. |
| 7,232,448 B2 | 6/2007 | Battles et al. |
| 7,255,675 B2 | 8/2007 | Gertner et al. |
| 7,261,709 B2 | 8/2007 | Swoyer et al. |
| 7,261,710 B2 | 8/2007 | Elmouelhi et al. |
| 7,282,020 B2 | 10/2007 | Kaplan |
| 7,288,063 B2 | 10/2007 | Petros et al. |
| 7,303,108 B2 | 12/2007 | Shelton |
| 7,320,701 B2 | 1/2008 | Haut et al. |
| 7,322,974 B2 | 1/2008 | Swoyer et al. |
| 7,326,221 B2 | 2/2008 | Sakamoto et al. |
| 7,334,822 B1 | 2/2008 | Hines |
| 7,335,197 B2 | 2/2008 | Sage et al. |
| 7,340,300 B2 | 3/2008 | Christopherson et al. |
| 7,399,304 B2 | 7/2008 | Gambale et al. |
| 7,402,166 B2 | 7/2008 | Feigl |
| 7,416,554 B2 | 8/2008 | Lam et al. |
| 7,417,175 B2 | 8/2008 | Oda et al. |
| 7,437,194 B2 | 10/2008 | Skwarek et al. |
| 7,463,934 B2 | 12/2008 | Tronnes et al. |
| 7,470,228 B2 | 12/2008 | Connors et al. |
| 7,481,771 B2 | 1/2009 | Fonseca et al. |
| 7,485,124 B2 | 2/2009 | Kuhns et al. |
| 7,553,317 B2 | 6/2009 | William et al. |
| 7,608,108 B2 | 10/2009 | Bhatnagar et al. |
| 7,632,297 B2 | 12/2009 | Gross |
| 7,645,286 B2 | 1/2010 | Catanese et al. |
| 7,658,311 B2 | 2/2010 | Boudreaux |
| 7,666,197 B2 | 2/2010 | Orban |
| 7,674,275 B2 | 3/2010 | Martin et al. |
| 7,682,374 B2 | 3/2010 | Foerster et al. |
| 7,695,494 B2 | 4/2010 | Foerster |
| 7,704,261 B2 | 4/2010 | Sakamoto et al. |
| 7,727,248 B2 | 6/2010 | Smith et al. |
| 7,731,725 B2 | 6/2010 | Gadberry et al. |
| 7,736,374 B2 | 6/2010 | Vaughan et al. |
| 7,758,594 B2 | 7/2010 | Lamson et al. |
| 7,766,923 B2 | 8/2010 | Catanese et al. |
| 7,766,939 B2 | 8/2010 | Yeung et al. |
| 7,780,682 B2 | 8/2010 | Catanese et al. |
| 7,815,655 B2 | 10/2010 | Catanese et al. |
| 7,850,712 B2 | 12/2010 | Conlon et al. |
| 7,862,584 B2 | 1/2011 | Lyons et al. |
| 7,887,551 B2 | 2/2011 | Bojarski et al. |
| 7,896,891 B2 | 3/2011 | Catanese et al. |
| 7,905,889 B2 | 3/2011 | Catanese et al. |
| 7,905,904 B2 | 3/2011 | Stone et al. |
| 7,909,836 B2 | 3/2011 | McLean et al. |
| 7,914,542 B2 | 3/2011 | Lamson et al. |
| 7,922,645 B2 | 4/2011 | Kaplan |
| 7,951,158 B2 | 5/2011 | Catanese et al. |
| 8,007,503 B2 | 8/2011 | Catanese et al. |
| 8,043,309 B2 | 10/2011 | Catanese et al. |
| 8,114,070 B2 | 2/2012 | Rubinsky et al. |
| 8,145,321 B2 | 3/2012 | Gross |
| 8,152,804 B2 | 4/2012 | Elmouelhi et al. |
| 8,157,815 B2 | 4/2012 | Catanese et al. |

(56) References Cited

U.S. PATENT DOCUMENTS

| | | |
|---|---|---|
| 8,162,960 B2 | 4/2012 | Manzo |
| 8,167,830 B2 | 5/2012 | Noriega |
| 8,211,118 B2 | 7/2012 | Catanese et al. |
| 8,216,254 B2 | 7/2012 | McLean et al. |
| 8,236,011 B2 | 8/2012 | Harris et al. |
| 8,251,985 B2 | 8/2012 | Hoey et al. |
| 8,273,079 B2 | 9/2012 | Hoey et al. |
| 8,298,132 B2 | 10/2012 | Connors et al. |
| 8,303,604 B2 | 11/2012 | Stone et al. |
| 8,308,765 B2 | 11/2012 | Saadat et al. |
| 8,333,776 B2 | 12/2012 | Cheng et al. |
| 8,343,187 B2 | 1/2013 | Lamson et al. |
| 8,361,112 B2 | 1/2013 | Kempton et al. |
| 8,372,065 B2 | 2/2013 | Hoey et al. |
| 8,388,611 B2 | 3/2013 | Shadduck et al. |
| 8,388,653 B2 | 3/2013 | Nobis et al. |
| 8,394,110 B2 | 3/2013 | Catanese et al. |
| 8,394,113 B2 | 3/2013 | Wei et al. |
| 8,419,723 B2 | 4/2013 | Shadduck et al. |
| 8,425,535 B2 | 4/2013 | McLean et al. |
| 8,444,657 B2 | 5/2013 | Saadat et al. |
| 8,454,655 B2 | 6/2013 | Yeung et al. |
| 8,465,551 B1 | 6/2013 | Wijay et al. |
| 8,480,686 B2 | 7/2013 | Bakos et al. |
| 8,491,606 B2 | 7/2013 | Tong et al. |
| 8,496,684 B2 | 7/2013 | Crainich et al. |
| 8,521,257 B2 | 8/2013 | Whitcomb et al. |
| 8,529,584 B2 | 9/2013 | Catanese et al. |
| 8,529,588 B2 | 9/2013 | Ahlberg et al. |
| 8,562,646 B2 | 10/2013 | Gellman et al. |
| 8,585,692 B2 | 11/2013 | Shadduck et al. |
| 8,603,106 B2 | 12/2013 | Catanese et al. |
| 8,603,123 B2 | 12/2013 | Todd |
| 8,603,187 B2 | 12/2013 | Kilemnick et al. |
| 8,628,542 B2 | 1/2014 | Merrick et al. |
| 8,663,243 B2 | 3/2014 | Lamson et al. |
| 8,668,705 B2 | 3/2014 | Johnston et al. |
| 8,683,895 B2 | 4/2014 | Nash |
| 8,715,239 B2 | 5/2014 | Lamson et al. |
| 8,715,298 B2 | 5/2014 | Catanese et al. |
| 8,734,469 B2 | 5/2014 | Pribanic et al. |
| 8,790,356 B2 | 7/2014 | Darois et al. |
| 8,801,702 B2 | 8/2014 | Hoey et al. |
| 8,808,363 B2 | 8/2014 | Perry et al. |
| 8,814,856 B2 | 8/2014 | Elmouelhi et al. |
| 8,828,035 B2 | 9/2014 | Kim |
| 8,834,458 B2 | 9/2014 | Neuberger et al. |
| 8,880,195 B2 | 11/2014 | Azure |
| 8,900,293 B2 | 12/2014 | Forbes et al. |
| 8,920,437 B2 | 12/2014 | Harris et al. |
| 8,926,494 B1 | 1/2015 | Cook et al. |
| 8,945,114 B2 | 2/2015 | Elmouelhi et al. |
| 9,034,001 B2 | 5/2015 | Cheng et al. |
| 9,039,740 B2 | 5/2015 | Wales et al. |
| 9,089,320 B2 | 7/2015 | Spivey et al. |
| 9,150,817 B2 | 10/2015 | Furihata et al. |
| 9,179,991 B2 | 11/2015 | Gozzi et al. |
| 9,204,922 B2 | 12/2015 | Hooven |
| 9,211,155 B2 | 12/2015 | Fruland et al. |
| 9,220,874 B2 | 12/2015 | Pillai et al. |
| 9,272,140 B2 | 3/2016 | Gerber |
| 9,277,914 B2 | 3/2016 | Wales et al. |
| 9,345,507 B2 | 5/2016 | Hoey et al. |
| 9,345,867 B2 | 5/2016 | Browning |
| 9,393,007 B2 | 7/2016 | Darois et al. |
| 9,439,643 B2 | 9/2016 | Darois et al. |
| 9,459,751 B2 | 10/2016 | Weaver et al. |
| 9,526,555 B2 | 12/2016 | Hoey et al. |
| 9,549,739 B2 | 1/2017 | Catanese et al. |
| 9,561,025 B2 | 2/2017 | Stone et al. |
| 9,592,044 B2 | 3/2017 | Weir et al. |
| 9,597,145 B2 | 3/2017 | Nelson et al. |
| 9,668,803 B2 | 6/2017 | Bhushan et al. |
| 9,675,373 B2 | 6/2017 | Todd |
| 9,750,492 B2 | 9/2017 | Ziniti et al. |
| 2001/0041916 A1 | 11/2001 | Bonutti |
| 2001/0044639 A1 | 11/2001 | Levinson |
| 2002/0049453 A1 | 4/2002 | Nobles et al. |
| 2002/0095064 A1 | 7/2002 | Beyar |
| 2002/0095154 A1 | 7/2002 | Atkinson et al. |
| 2002/0107540 A1 | 8/2002 | Whalen et al. |
| 2002/0128684 A1 | 9/2002 | Foerster |
| 2002/0161382 A1 | 10/2002 | Neisz et al. |
| 2002/0177866 A1 | 11/2002 | Weikel et al. |
| 2002/0183740 A1 | 12/2002 | Edwards et al. |
| 2002/0193809 A1 | 12/2002 | Meade et al. |
| 2003/0023248 A1 | 1/2003 | Parodi |
| 2003/0040803 A1 | 2/2003 | Rioux et al. |
| 2003/0060819 A1 | 3/2003 | McGovern et al. |
| 2003/0078601 A1 | 4/2003 | Shikhman et al. |
| 2003/0109769 A1 | 6/2003 | Lowery et al. |
| 2003/0120309 A1 | 6/2003 | Colleran et al. |
| 2003/0130575 A1 | 7/2003 | Desai |
| 2003/0144570 A1 | 7/2003 | Hunter et al. |
| 2003/0176883 A1 | 9/2003 | Sauer et al. |
| 2003/0191497 A1 | 10/2003 | Cope |
| 2003/0199860 A1 | 10/2003 | Loeb et al. |
| 2003/0204195 A1 | 10/2003 | Keane et al. |
| 2003/0236535 A1 | 12/2003 | Onuki et al. |
| 2004/0010301 A1 | 1/2004 | Kindlein et al. |
| 2004/0030217 A1 | 2/2004 | Yeung et al. |
| 2004/0043052 A1 | 3/2004 | Hunter et al. |
| 2004/0044350 A1 | 3/2004 | Martin et al. |
| 2004/0078046 A1 | 4/2004 | Barzell et al. |
| 2004/0122456 A1 | 6/2004 | Saadat et al. |
| 2004/0122474 A1 | 6/2004 | Gellman et al. |
| 2004/0143343 A1 | 7/2004 | Grocela |
| 2004/0147958 A1 | 7/2004 | Lam et al. |
| 2004/0162568 A1 | 8/2004 | Saadat et al. |
| 2004/0167635 A1 | 8/2004 | Yachia et al. |
| 2004/0172046 A1 | 9/2004 | Hlavka et al. |
| 2004/0193191 A1 | 9/2004 | Starksen et al. |
| 2004/0193194 A1 | 9/2004 | Laufer et al. |
| 2004/0193196 A1 | 9/2004 | Appling et al. |
| 2004/0194790 A1 | 10/2004 | Laufer et al. |
| 2004/0215181 A1 | 10/2004 | Christopherson et al. |
| 2004/0230316 A1 | 11/2004 | Cioanta et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0243227 A1 | 12/2004 | Starksen et al. |
| 2004/0260345 A1 | 12/2004 | Foerster |
| 2005/0010203 A1 | 1/2005 | Edwards et al. |
| 2005/0033403 A1 | 2/2005 | Ward et al. |
| 2005/0055087 A1 | 3/2005 | Starksen |
| 2005/0059929 A1 | 3/2005 | Bolmsjo et al. |
| 2005/0065550 A1 | 3/2005 | Starksen et al. |
| 2005/0101982 A1 | 5/2005 | Ravenscroft et al. |
| 2005/0107811 A1 | 5/2005 | Starksen et al. |
| 2005/0107812 A1 | 5/2005 | Starksen et al. |
| 2005/0137716 A1 | 6/2005 | Gross |
| 2005/0154401 A1 | 7/2005 | Weldon et al. |
| 2005/0165272 A1 | 7/2005 | Okada et al. |
| 2005/0171522 A1 | 8/2005 | Christopherson |
| 2005/0177181 A1 | 8/2005 | Kagan et al. |
| 2005/0203344 A1 | 9/2005 | Orban et al. |
| 2005/0203550 A1 | 9/2005 | Laufer et al. |
| 2005/0216040 A1 | 9/2005 | Gertner et al. |
| 2005/0216078 A1 | 9/2005 | Starksen et al. |
| 2005/0222557 A1 | 10/2005 | Baxter et al. |
| 2005/0251157 A1 | 11/2005 | Saadat et al. |
| 2005/0251159 A1 | 11/2005 | Ewers et al. |
| 2005/0251177 A1 | 11/2005 | Saadat et al. |
| 2005/0251206 A1 | 11/2005 | Maahs et al. |
| 2005/0267405 A1 | 12/2005 | Shah |
| 2005/0273138 A1 | 12/2005 | To et al. |
| 2005/0283189 A1 | 12/2005 | Rosenblatt |
| 2005/0288694 A1 | 12/2005 | Solomon |
| 2006/0004410 A1 | 1/2006 | Nobis et al. |
| 2006/0020276 A1 | 1/2006 | Saadat et al. |
| 2006/0020327 A1 | 1/2006 | Lashinski et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |

(56) References Cited

U.S. PATENT DOCUMENTS

| | | |
|---|---|---|
| 2006/0025819 A1 | 2/2006 | Nobis et al. |
| 2006/0026750 A1 | 2/2006 | Ballance |
| 2006/0030884 A1 | 2/2006 | Yeung et al. |
| 2006/0058817 A1 | 3/2006 | Starksen et al. |
| 2006/0079880 A1 | 4/2006 | Sage et al. |
| 2006/0079881 A1 | 4/2006 | Christopherson et al. |
| 2006/0089646 A1 | 4/2006 | Bonutti |
| 2006/0095058 A1 | 5/2006 | Sivan et al. |
| 2006/0167477 A1 | 7/2006 | Arcia et al. |
| 2006/0178680 A1 | 8/2006 | Nelson et al. |
| 2006/0199996 A1 | 9/2006 | Caraballo et al. |
| 2006/0241694 A1 | 10/2006 | Cerundolo |
| 2006/0265042 A1 | 11/2006 | Catanese et al. |
| 2006/0271032 A1 | 11/2006 | Chin et al. |
| 2006/0276481 A1 | 12/2006 | Evrard et al. |
| 2006/0276871 A1 | 12/2006 | Lamson et al. |
| 2006/0282081 A1 | 12/2006 | Fanton et al. |
| 2007/0049929 A1 | 3/2007 | Catanese et al. |
| 2007/0049970 A1 | 3/2007 | Belef et al. |
| 2007/0060931 A1 | 3/2007 | Hamilton et al. |
| 2007/0073322 A1 | 3/2007 | Mikkaichi et al. |
| 2007/0073342 A1 | 3/2007 | Stone et al. |
| 2007/0088362 A1 | 4/2007 | Bonutti et al. |
| 2007/0100421 A1 | 5/2007 | Griffin |
| 2007/0112385 A1 | 5/2007 | Conlon |
| 2007/0142846 A1 | 6/2007 | Catanese et al. |
| 2007/0173888 A1 | 7/2007 | Gertner et al. |
| 2007/0179491 A1 | 8/2007 | Kratoska et al. |
| 2007/0179496 A1 | 8/2007 | Swoyer et al. |
| 2007/0198038 A1 | 8/2007 | Cohen et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0021485 A1 | 1/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039893 A1 | 2/2008 | McLean et al. |
| 2008/0039894 A1 | 2/2008 | Catanese et al. |
| 2008/0039921 A1 | 2/2008 | Wallsten et al. |
| 2008/0045978 A1 | 2/2008 | Kuhns et al. |
| 2008/0051810 A1 | 2/2008 | To et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0161852 A1 | 7/2008 | Kaiser et al. |
| 2008/0195145 A1 | 8/2008 | Bonutti et al. |
| 2008/0208220 A1 | 8/2008 | Shiono et al. |
| 2008/0228202 A1 | 9/2008 | Cropper et al. |
| 2008/0269737 A1 | 10/2008 | Elmouelhi et al. |
| 2009/0012537 A1 | 1/2009 | Green |
| 2009/0018553 A1 | 1/2009 | McLean et al. |
| 2009/0060977 A1 | 3/2009 | Lamson et al. |
| 2009/0112234 A1 | 4/2009 | Crainich et al. |
| 2009/0112537 A1 | 4/2009 | Okumura |
| 2009/0118762 A1 | 5/2009 | Crainch et al. |
| 2009/0177288 A1 | 7/2009 | Wallsten |
| 2009/0198227 A1 | 8/2009 | Prakash |
| 2010/0010631 A1 | 1/2010 | Otte et al. |
| 2010/0023022 A1 | 1/2010 | Zeiner et al. |
| 2010/0023024 A1 | 1/2010 | Zeiner et al. |
| 2010/0023025 A1 | 1/2010 | Zeiner et al. |
| 2010/0023026 A1 | 1/2010 | Zeiner et al. |
| 2010/0030262 A1 | 2/2010 | McLean et al. |
| 2010/0030263 A1 | 2/2010 | Cheng et al. |
| 2010/0049188 A1 | 2/2010 | Nelson et al. |
| 2010/0063542 A1 | 3/2010 | Burg et al. |
| 2010/0114162 A1 | 5/2010 | Bojarski et al. |
| 2010/0130815 A1 | 5/2010 | Gross et al. |
| 2010/0286106 A1 | 11/2010 | Gat et al. |
| 2010/0286679 A1 | 11/2010 | Hoey et al. |
| 2010/0298948 A1 | 11/2010 | Hoey et al. |
| 2010/0324669 A1 | 12/2010 | Hlavka et al. |
| 2011/0040312 A1 | 2/2011 | Lamson et al. |
| 2011/0046648 A1 | 2/2011 | Johnston et al. |
| 2011/0060349 A1 | 3/2011 | Cheng et al. |
| 2011/0077676 A1 | 3/2011 | Sivan et al. |
| 2011/0144423 A1 | 6/2011 | Tong et al. |
| 2011/0152839 A1 | 6/2011 | Cima et al. |
| 2011/0160747 A1 | 6/2011 | McLean et al. |
| 2011/0166564 A1 | 7/2011 | Merrick et al. |
| 2011/0190758 A1 | 8/2011 | Lamson et al. |
| 2011/0196393 A1 | 8/2011 | Eliachar et al. |
| 2011/0202052 A1 | 8/2011 | Gelbart et al. |
| 2011/0218387 A1 | 9/2011 | Lamson et al. |
| 2011/0245828 A1 | 10/2011 | Baxter et al. |
| 2011/0276081 A1 | 11/2011 | Kilemnik |
| 2011/0276086 A1 | 11/2011 | Al-Qbandi et al. |
| 2012/0010645 A1 | 1/2012 | Feld |
| 2012/0059387 A1 | 3/2012 | Schanz et al. |
| 2012/0165837 A1 | 6/2012 | Belman et al. |
| 2012/0203250 A1 | 8/2012 | Weir et al. |
| 2012/0245600 A1 | 9/2012 | McLean et al. |
| 2012/0265006 A1 | 10/2012 | Makower et al. |
| 2013/0096582 A1 | 4/2013 | Cheng et al. |
| 2013/0178871 A1 | 7/2013 | Koogle et al. |
| 2013/0211431 A1 | 8/2013 | Wei et al. |
| 2013/0253574 A1 | 9/2013 | Catanese et al. |
| 2013/0253662 A1 | 9/2013 | Lamson et al. |
| 2013/0261383 A1 | 10/2013 | Catanese et al. |
| 2013/0261665 A1 | 10/2013 | Yeung et al. |
| 2013/0267772 A1 | 10/2013 | Catanese et al. |
| 2013/0268001 A1 | 10/2013 | Catanese et al. |
| 2013/0274799 A1 | 10/2013 | Catanese et al. |
| 2013/0289342 A1 | 10/2013 | Tong et al. |
| 2013/0296639 A1 | 11/2013 | Lamson et al. |
| 2013/0296889 A1 | 11/2013 | Tong et al. |
| 2013/0296935 A1 | 11/2013 | McLean et al. |
| 2013/0325143 A1 | 12/2013 | Lamson et al. |
| 2014/0005473 A1 | 1/2014 | Catanese et al. |
| 2014/0005690 A1 | 1/2014 | Catanese et al. |
| 2014/0012192 A1* | 1/2014 | Bar-On ............... A61F 2/04 604/93.01 |
| 2014/0088587 A1 | 3/2014 | Merrick et al. |
| 2014/0221981 A1 | 8/2014 | Cima et al. |
| 2014/0236230 A1 | 8/2014 | Johnston et al. |
| 2014/0288637 A1 | 9/2014 | Clerc et al. |
| 2015/0112299 A1 | 4/2015 | Forbes et al. |
| 2015/0157309 A1 | 6/2015 | Bird |
| 2015/0257908 A1 | 9/2015 | Chao et al. |
| 2015/0335393 A1 | 11/2015 | Ciulla et al. |
| 2016/0000455 A1 | 1/2016 | Golan et al. |
| 2016/0038087 A1 | 2/2016 | Hunter |
| 2016/0051735 A1 | 2/2016 | Slepian |
| 2016/0081736 A1 | 3/2016 | Hoey et al. |
| 2016/0089140 A1 | 3/2016 | Kawaura et al. |
| 2016/0096009 A1 | 4/2016 | Feld |
| 2016/0120647 A1 | 5/2016 | Rogers et al. |
| 2016/0206370 A1 | 7/2016 | Fruland et al. |
| 2016/0242894 A1 | 8/2016 | Davis |
| 2016/0302904 A1 | 10/2016 | Ogdahl et al. |
| 2016/0317180 A1 | 11/2016 | Kilemnik |
| 2017/0000598 A1 | 1/2017 | Bachar |
| 2017/0128741 A1 | 5/2017 | Keltner et al. |
| 2017/0135830 A1 | 5/2017 | Harkin et al. |

FOREIGN PATENT DOCUMENTS

| | | |
|---|---|---|
| CN | 101795641 A | 8/2010 |
| CN | 102112064 B | 6/2014 |
| CN | 105919695 A | 9/2016 |
| DE | 10159470 A1 | 6/2003 |
| EP | 0246836 B1 | 12/1991 |
| EP | 0464480 A1 | 1/1992 |
| EP | 0274846 B1 | 2/1994 |
| EP | 0632999 A1 | 1/1995 |

(56) References Cited

FOREIGN PATENT DOCUMENTS

| | | |
|---|---|---|
| EP | 0667126 A1 | 8/1995 |
| EP | 1016377 A2 | 7/2000 |
| EP | 1482841 A1 | 12/2004 |
| EP | 1082941 B1 | 3/2005 |
| EP | 1584295 A2 | 10/2005 |
| EP | 1006909 B1 | 1/2007 |
| EP | 1852071 A2 | 11/2007 |
| EP | 1584295 B1 | 2/2008 |
| EP | 1884198 A2 | 2/2008 |
| EP | 1884199 A1 | 2/2008 |
| EP | 1670361 B1 | 4/2008 |
| EP | 1331886 B1 | 12/2008 |
| EP | 1482840 B1 | 12/2008 |
| EP | 2243507 A1 | 10/2010 |
| EP | 1484023 B1 | 5/2011 |
| EP | 2345373 A1 | 7/2011 |
| EP | 2345374 A1 | 7/2011 |
| EP | 2049023 B1 | 12/2014 |
| EP | 3167845 A1 | 5/2017 |
| FR | 2750031 A1 | 12/1997 |
| JP | 5836559 A | 3/1983 |
| JP | 09122134 | 5/1997 |
| JP | 3370300 B2 | 1/2003 |
| JP | 2004344427 A | 12/2004 |
| JP | 2009521278 A | 6/2009 |
| JP | 2011529745 A | 12/2011 |
| JP | 2012143622 A | 8/2012 |
| KR | 20060009698 A | 2/2006 |
| RU | 2062121 C1 | 6/1996 |
| RU | 2112571 C1 | 6/1998 |
| RU | 2128012 C1 | 3/1999 |
| RU | 2221501 C2 | 1/2004 |
| SU | 825094 A1 | 4/1981 |
| WO | 1987001270 A1 | 3/1987 |
| WO | 1992010142 A1 | 6/1992 |
| WO | 1993004727 A1 | 3/1993 |
| WO | 1993015664 A1 | 8/1993 |
| WO | 1995000818 A1 | 1/1995 |
| WO | 2000040159 A1 | 7/2000 |
| WO | 2001026588 A2 | 4/2001 |
| WO | 2001028432 A1 | 4/2001 |
| WO | 2001039671 A1 | 6/2001 |
| WO | 2001049195 A1 | 7/2001 |
| WO | 2001095818 A1 | 12/2001 |
| WO | 2002028289 A1 | 4/2002 |
| WO | 2002030335 A2 | 4/2002 |
| WO | 2002032321 A1 | 4/2002 |
| WO | 2002058577 A1 | 8/2002 |
| WO | 2003039334 A2 | 5/2003 |
| WO | 2003077772 A1 | 9/2003 |
| WO | 2004000159 A2 | 12/2003 |
| WO | 2004017845 A1 | 3/2004 |
| WO | 2004019787 A2 | 3/2004 |
| WO | 2004019788 A2 | 3/2004 |
| WO | 2004030569 A2 | 4/2004 |
| WO | 2004066875 A1 | 8/2004 |
| WO | 2004080529 A2 | 9/2004 |
| WO | 2004103189 A1 | 12/2004 |
| WO | 2005034738 A2 | 4/2005 |
| WO | 2005065412 A2 | 7/2005 |
| WO | 2005094447 A2 | 10/2005 |
| WO | 2006127241 A2 | 11/2006 |
| WO | 2006127431 A2 | 11/2006 |
| WO | 2007048274 A1 | 5/2007 |
| WO | 2007053516 A2 | 5/2007 |
| WO | 2007064906 A2 | 6/2007 |
| WO | 2007075981 A2 | 7/2007 |
| WO | 2008002340 A1 | 1/2008 |
| WO | 2008006084 A2 | 1/2008 |
| WO | 2008014191 A2 | 1/2008 |
| WO | 2008043044 A2 | 4/2008 |
| WO | 2008043917 A2 | 4/2008 |
| WO | 2008097942 A1 | 8/2008 |
| WO | 2008132735 A1 | 11/2008 |
| WO | 2008142677 A2 | 11/2008 |
| WO | 2009009617 A1 | 1/2009 |
| WO | 2009072131 A2 | 6/2009 |
| WO | 2010011832 A1 | 1/2010 |
| WO | 2010014821 A2 | 2/2010 |
| WO | 2010014825 A1 | 2/2010 |
| WO | 2010065214 A2 | 6/2010 |
| WO | 2010086849 A1 | 8/2010 |
| WO | 2010106543 A2 | 9/2010 |
| WO | 2011084712 A1 | 7/2011 |
| WO | 2012018446 A2 | 2/2012 |
| WO | 2012079548 A1 | 6/2012 |
| WO | 2012079549 A2 | 6/2012 |
| WO | 2012091952 A2 | 7/2012 |
| WO | 2012091954 A2 | 7/2012 |
| WO | 2012091955 A2 | 7/2012 |
| WO | 2012091956 A2 | 7/2012 |
| WO | 2012123950 A2 | 9/2012 |
| WO | 2014003987 A1 | 1/2014 |
| WO | 2014035506 A2 | 3/2014 |
| WO | 2014145381 A1 | 9/2014 |
| WO | 2014153219 A1 | 9/2014 |
| WO | 2014200764 A1 | 12/2014 |
| WO | 2015101975 A1 | 7/2015 |
| WO | 2016134166 A1 | 8/2016 |
| WO | 2017017499 A1 | 2/2017 |
| WO | 2017081326 A2 | 5/2017 |
| WO | 2017112856 A1 | 6/2017 |

OTHER PUBLICATIONS

Berges, Richard, et al. "Alternative Minimalinvasive Therapien Beim Benignen Prostatasyndrom", Medizin, Jg. 104, Heft 37, Sep. 14, 2007.

Borzhievski, et al., "Tactics of the Surgical Treatment of Patients With Prostatic Adenoma and Acute Urinary Retention," Urologia Nefrol (Mosk), Jan.-Feb. 1987, (1):39-43.

European Search Report for EP Application No. 06770621.8, dated Sep. 20, 2012.

European Search Report for EP Application No. 06845991.6, dated Mar. 22, 2013.

European Search Report for EP Application No. 07840462.1, dated May 29, 2012.

European Search Report for EP Application No. 08729001.1, dated Feb. 4, 2014.

European Search Report for EP Application No. 08772483.7, dated Feb. 12, 2015.

European Search Report for EP Application No. 11154962.2, dated May 19, 2011.

European Search Report for EP Application No. 11154976.2, dated Jun. 6, 2011.

European Search Report for EP Application No. 11814950.9, dated Sep. 8, 2015.

European Search Report for EP Application No. 11852778.7, dated Nov. 19, 2015.

European Search Report for EP Application No. 11854148.1, dated Oct. 20, 2017.

European Search Report for EP Application No. 13810314.8, dated Apr. 6, 2016.

European Search Report for EP Application No. 17150545.6, dated Sep. 11, 2017.

Hartung, Rudolf, et al. "Instrumentelle Therapie der benignen Prostatahyperplasie", Medizin, Deutsches Arzteblatt 97, Heft 15, Apr. 14, 2000.

Hofner, Klaus, et al., "Operative Therapie des benignen Prostatasyndroms", Medizin, Dtsch Arztebl, 2007; 104(36):A 2424-9.

Hubmann, R. "Geschichte der transurethralen Prostataeingriffe", Geschichte der Medizin, Urologe [B], 2000, 40:152-160.

International Search Report for PCT Application No. PCT/US2006/019372, dated May 2, 2008.

International Search Report for PCT Application No. PCT/US2006/048962, dated Dec. 10, 2008.

International Search Report for PCT Application No. PCT/US2007/074019, dated Jul. 25, 2008.

(56) References Cited

OTHER PUBLICATIONS

International Search Report for PCT Application No. PCT/US2008/053001, dated Jun. 17, 2008.
International Search Report for PCT Application No. PCT/US2008/069560, dated Sep. 8, 2008.
International Search Report for PCT Application No. PCT/US2009/052271, dated Apr. 7, 2010.
International Search Report for PCT Application No. PCT/US2009/052275, dated Oct. 9, 2009.
International Search Report for PCT Application No. PCT/US2011/041200, dated Feb. 17, 2012.
International Search Report for PCT Application No. PCT/US2011/065348, dated Jun. 21, 2012.
International Search Report for PCT Application No. PCT/US2011/065358, dated Jun. 21, 2012.
International Search Report for PCT Application No. PCT/US2011/065377, dated Aug. 29, 2012.
International Search Report for PCT Application No. PCT/US2011/065386, dated Jun. 28, 2012.
International Search Report for PCT Application No. PCT/US2013/044035, dated Sep. 6, 2013.
Jonas, U., et al., "Benigne Prostatahyperplasie", Der Urologe 2006—[Sonderheft] 45:134-144.
Kruck, S., et al., "Aktuelle Therapiemoglichkeiten des Benignen Prostata—Syndroms", J Urol Urogynakol, 2009; 16(1): 19-22.
Miyake, Osamu. "Medical Examination and Treatment for BPH," Pharma Med, vol. 22, No. 3, 2004, p. 97-103.
Reich, O., et al., "Benignes Prostatasyndrom (BPS)," Der Urologe A Issue vol. 45, No. 6, Jun. 2006, p. 769-782.
Schauer, P., et al. "New applications for endoscopy: the emerging field of endoluminal and transgastric bariatric surgery", Surgical Endoscopy, (Apr. 24, 2006), 10 pgs.
Sharp, Howard T., M.D., et al. "Instruments and Methods—The 4-S Modification of the Roeder Knot: How to Tie It", Obstetrics & Gynecology, p. 1004-1006, vol. 90, No. 6, Dec. 1997.
Takashi, Daito. "Low-Invasive Treatment for BPH", Medico vol. 34, No. 10, p. 366-369, 2000.
Teruhisa, Ohashi. "Urinary Dysfunction by Lower Urinary Tract Obstruction in Male", Pharma Medica, vol. 8, No. 8, p. 35-39, 1990.
Tomohiko, Koyanagi, et al., "Surgery View of 21st Century," Urological Surgery, vol. 84, No. 1, p. 47-53, 2001.
Trapeznikov, et al., "New Technologies in the Treatment of Benign Prostatic Hyperplasia", Urologia Nefrol (Mosk), Jul.-Aug. 1996, (4):41-47.
Yeung, Jeff. "Treating Urinary Stress Incontenance Without Incision with Endoscopic Suture Anchor & Approximating Device," Aleeva Medical, Inc., 2007.

* cited by examiner

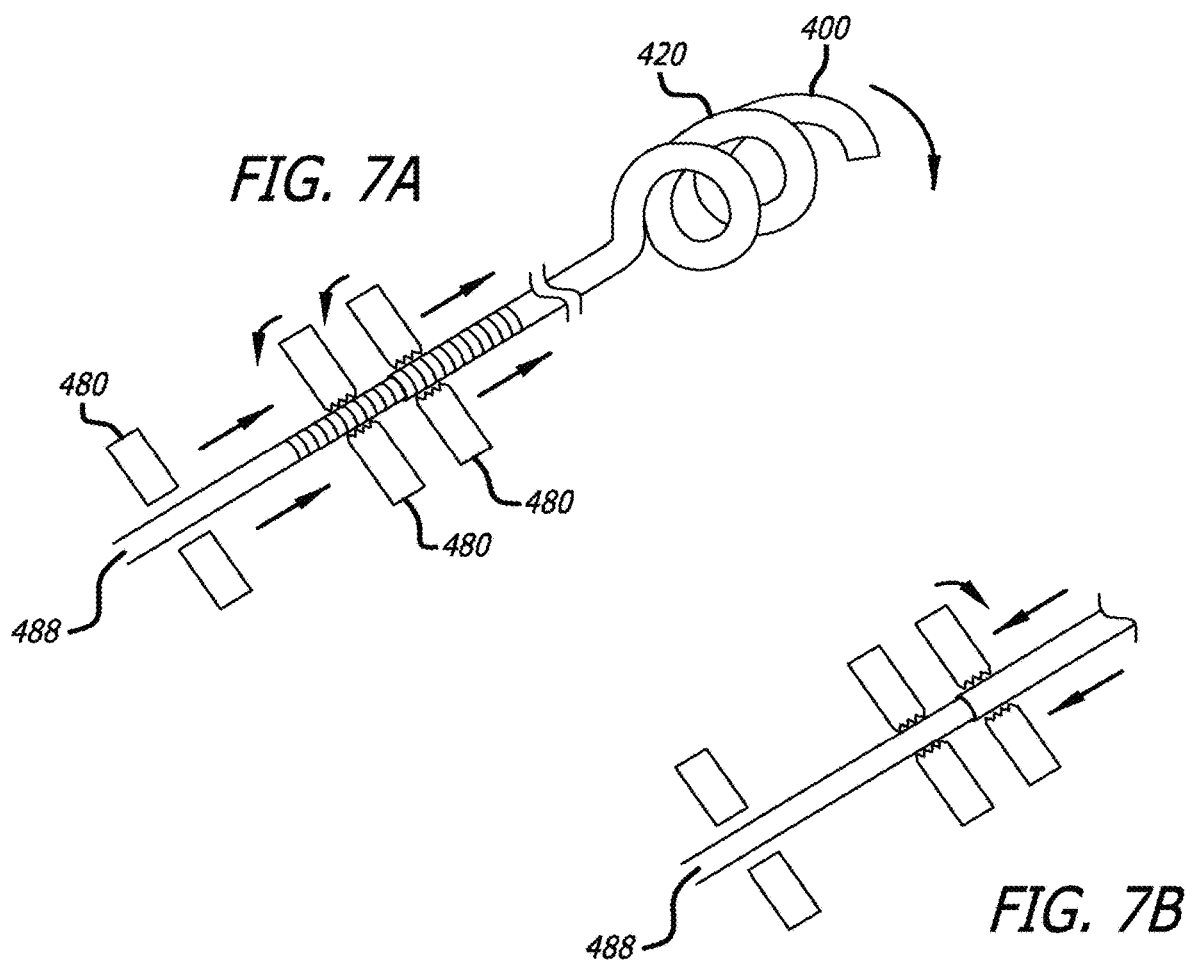
FIG. 7A
FIG. 7B
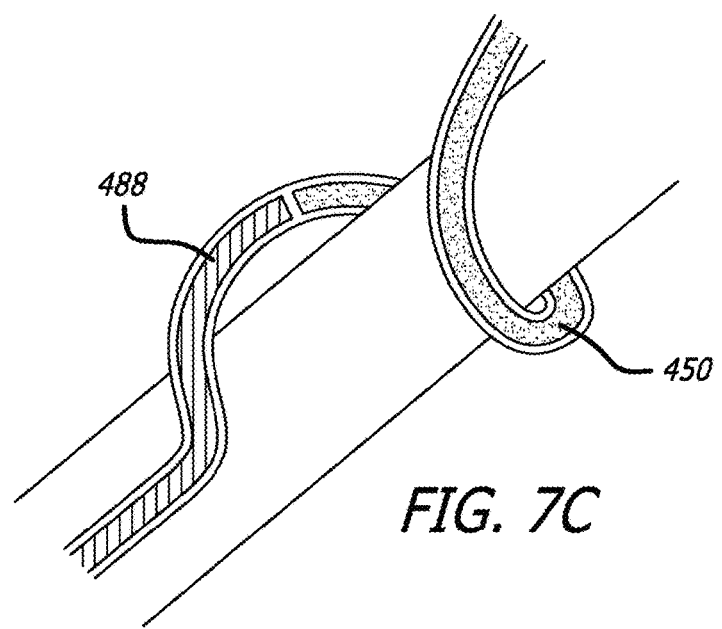
FIG. 7C

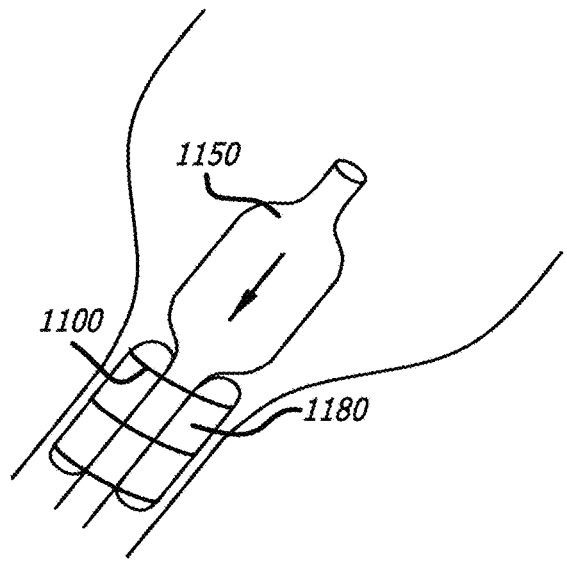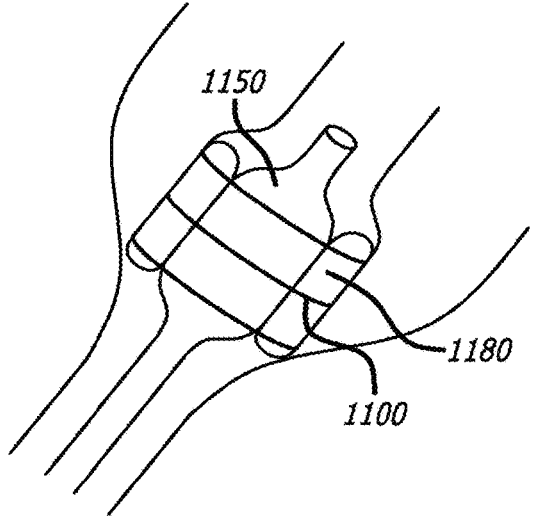
FIG. 15A FIG. 15B
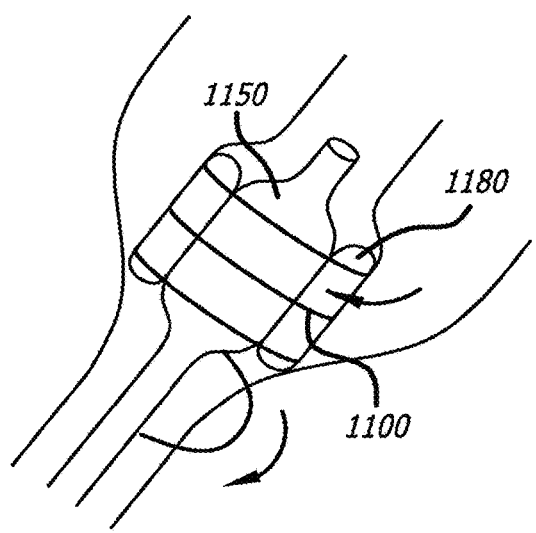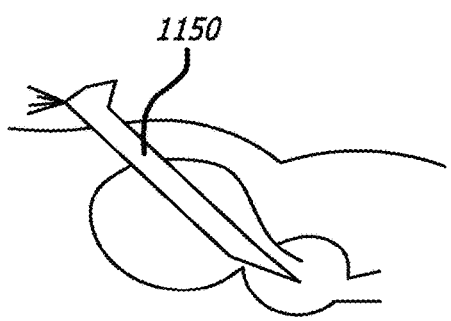
FIG. 15C FIG. 16

DEVICES, SYSTEMS AND METHODS FOR TREATING BENIGN PROSTATIC HYPERPLASIA AND OTHER CONDITIONS

CROSS-REFERENCE TO RELATED APPLICATIONS

This application is a continuation of U.S. application Ser. No. 16/234,282, filed Dec. 27, 2018, which is a continuation of U.S. application Ser. No. 13/830,811, filed Mar. 14, 2013, now U.S. Pat. No. 10,195,014, both entitled "Devices, Systems and Methods for Treating Benign Prostatic Hyperplasia and Other Conditions," and each of which is expressly incorporated herein by reference.

BACKGROUND

The present invention relates generally to medical devices and methods and more particularly to devices, systems and methods for treating conditions wherein a tissue (e.g., the prostate gland) has a) become enlarged and/or b) undergone a change in form, position, structure, rigidity or force exertion with respect to another anatomical structure and/or c) has begun to impinge upon or compress an adjacent anatomical structure (e.g., the urethra).

Benign Prostatic Hyperplasia (BPH) is one of the most common medical conditions that affect men, especially elderly men. It has been reported that, in the United States more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

Despite extensive efforts in both the medical device and pharmaco-therapeutic fields, current treatments remain only partially effective and are burdened with significant side effects. Certain devices used to displace urethral tissue, such as urethral stents, can become encrusted due to exposure to urine. This encrustation is an undesirable and problematic side effect.

Thus, there remains a need for the development of new devices, systems and methods for treating BPH as well as other conditions in which one tissue or anatomical structure impinges upon or compresses another tissue or anatomical structure.

SUMMARY

Certain embodiments related to a system for enlarging a lumen of a prostatic urethra. The system includes a delivery tool and an implant carried by the delivery tool. The implant is shaped to at least partially circumscribe the prostatic urethra of a patient. The system also includes a depth guide. The depth guide and delivery tool cooperate to deploy the implant within the peri-urethral space and thereby enlarge the lumen of the prostatic urethra.

In some embodiments, the delivery tool has a sharp surface configured to penetrate the urethral wall. In some embodiments, delivery tool delivers energy to prostatic tissue. In some embodiments, the implant has a sharp surface configured to penetrate the urethral wall. In some embodiments, the implant is carried externally to at least part of the delivery tool. In some embodiments, the implant is carried internally to at least part of the delivery tool. In some embodiments, the system includes a pusher coupled to the implant. In some embodiments, the system includes a locking mechanism coupled to at least one of the delivery tool, the implant, or the pusher. In some embodiments, the implant includes a first section and a second section, and the first section is comparatively more flexible than the second section. In some embodiments, the implant is self expanding. In some embodiments, the delivery tool and the implant each have a radius of curvature and the delivery tool radius of curvature is greater than the implant radius of curvature. In some embodiments, the implant includes a first section and a second section, and the first section is frictionally-engaged with the second section. In some embodiments, the implant is configured to be deployed by overcoming the frictional engagement.

BRIEF DESCRIPTION OF THE DRAWINGS

FIGS. 7A through 7C illustrate views of a method for placing an implant that is contained within a delivery tool according to an embodiment. A pusher and locking mechanisms facilitate delivery of the implant.

FIGS. 15A through 15C illustrate views of an embodiment in which the implant is placed using an expanding delivery member that is expanded within the bladder.

FIG. 16 illustrates a view of a supra pubic implant delivery method according to an embodiment.

DETAILED DESCRIPTION

Figure 1A:
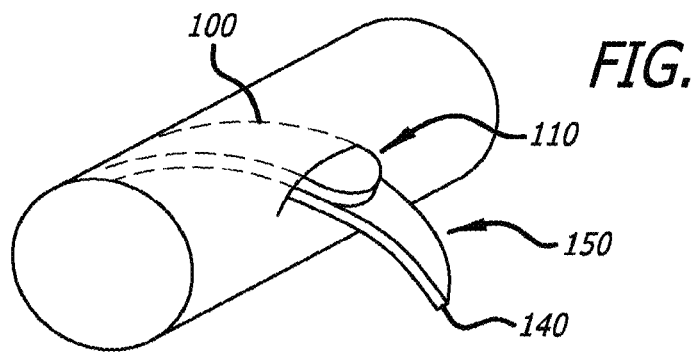
FIGS. 1A and 1B illustrate views of an embodiment in which a depth guide facilitates the delivery of an implant.

The following description of the preferred embodiments of the invention is not intended to limit the invention to these preferred embodiments, but rather to enable any person skilled in the art to make and use this invention. Disclosed herein are systems and methods for treating conditions wherein a tissue (e.g., the prostate gland) has a) become enlarged and/or b) undergone a change in form, position, structure, rigidity or force exertion with respect to another anatomical structure and/or c) has begun to impinge upon or compress an adjacent anatomical structure (e.g., the urethra).

Mechanically displacing prostatic tissue so as to enlarge the lumen of the prostatic urethra is an attractive long-term solution to BPH. However, as described above, chronic exposure of an implant to urine is undesirable. According to embodiments described herein, implants placed near the urethral boundary of the prostate can provide the mechanical forces necessary to enlarge the lumen of the prostatic urethra while avoiding chronic exposure to urine.

For the purposes of this application, the area of the prostate gland near the urethral surface can be referred to as the extra-urethral portion of the prostate. The extra-urethral portion of the prostate is also that portion of the prostate near enough to the urethral boundary such that the prostatic tissue is comparatively less spongy than the central part of the gland. The extra-urethral portion has sufficient mechanical integrity to hold an implant substantially in place. Because the size, shape, and tissue properties of the prostate can vary significantly from one subject to another, this application defines the extra-urethral region in terms of an approximate position relative to the prostatic urethra and in terms of the mechanical properties of the region. The extra-urethral region may also include, or be referred to as, the urethral wall without being limited exclusively to the membrane layer of the prostate immediately adjacent the prostatic urethra. The extra-urethral region may also include, or be referred to as, the peri-urethral region or peri-urethral tissue. Of course, in this application peri-urethral tissue still refers to the region of the urethra within the prostate.

Certain embodiments described herein place implants in the prostate by puncturing, cutting, dissecting, or otherwise penetrating the extra-urethral region of the prostate. In doing so, it is important to avoid puncturing the anatomy in undesirable locations, such as the urethral sphincter, the bladder, and ejaculation ducts. In certain embodiments, more than one extra-urethral implant is desirable to avoid puncturing such locations in the anatomy. For example, multiple implants could be placed such that one implant is distal to the ejaculation ducts and another implant is proximal to the ejaculation ducts. In this way, multiple implants can be used to provide the necessary mechanical dilation of and long-term stability in the urethral lumen while not substantially damaging sensitive parts of the local anatomy.

In certain embodiments, extra-urethral implants include cutting surfaces to facilitate delivery of the implant into tissue. Other surfaces of any delivery device used may be comparatively blunt such that the cutting is focused at a certain surface of the implant.

In certain embodiments, a delivery tool, member, and/or surface is used to cut, penetrate, dissect, separate, or otherwise provide a point of entry and optionally a path through tissue for an implant. In such embodiments, the delivery tool, member, and/or surface can be sharp, pointed, serrated, or otherwise configured to cut tissue. Further, the delivery tool, member, and/or surface can be configured to instead, or in addition, delivery energy (e.g., radio frequency, ultrasound, and/or laser) to tissue to accomplish the penetration.

Figure 1B:
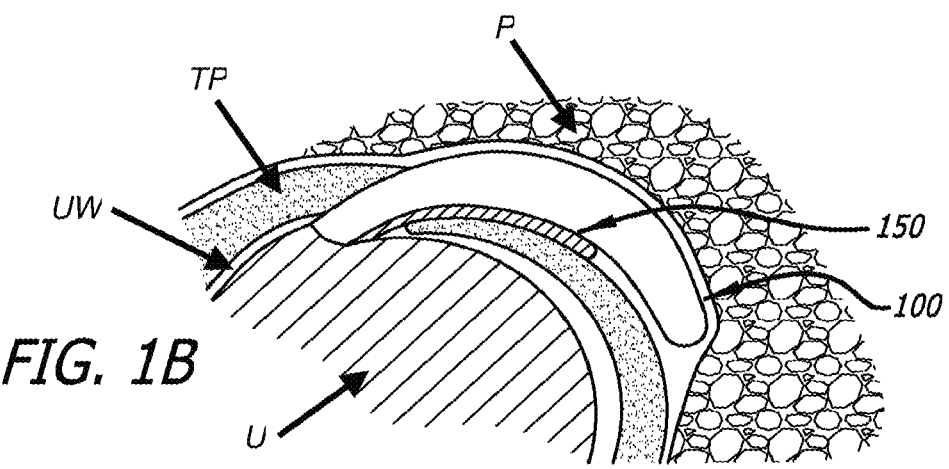

In certain embodiments, it is preferable to use selective blunt dissection in the peri-urethral tissue plane TP. In such embodiments, the blunt edges of a dissection tool or of the implant produce blunt dissection in the peri-urethral tissue plane TP, separating the urethra U from portions of the prostate P. A penetrating tip may be used to exit the urethra U and set the depth of the penetration such that the appropriate tissue plane in the extra-urethral region can be accessed. FIGS. 1A and 1B depict the blunt tip 110 of an extra-urethral implant 100 and the tip 140 of a depth guide 150 deployed to an adjustable depth alongside the blunt tip 110. The depth guide 150 ensures delivery of the extra-urethral implant 100 beyond the urethral wall UW by creating space between the implant and the urethral wall UW. The depth guide 150 can be withdrawn at any point during the implantation of the extra-urethral implant 100. Preferably, the depth guide 150 is kept in place until the extra-urethral implant 100 has been deployed in the extra-urethral region such that the extra-urethral implant 100 mechanically displaces prostatic tissue away from the urethral lumen. The depth guide 150 can be removably fastened to the extra-urethral implant 100 by various methods. For example, the depth guide 150 can be fastened with one way tabs such that the depth guide 150 remains fixed to the extra-urethral implant 100 when the two members are pushed but can be released from in gauge meant with the extra-urethral implant 100 when the depth guide 150 is pulled proximally and the extra-urethral implant 100 is held in place. Other equivalent methods are within the scope of this disclosure.

In certain embodiments, the extra-urethral implant is delivered such that it is "wound up" like a spring prior to delivery. Upon removal of the depth guide 150, the implant 100 is configured to unwind and expand its diameter.

Figure 2:
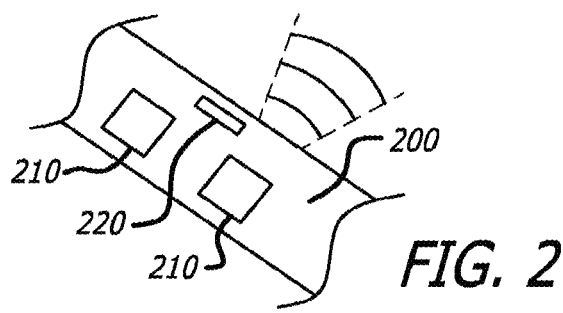
FIG. 2 illustrates views of an embodiment in which transmitters and receivers help determine the position of an implant.
Figure 3:
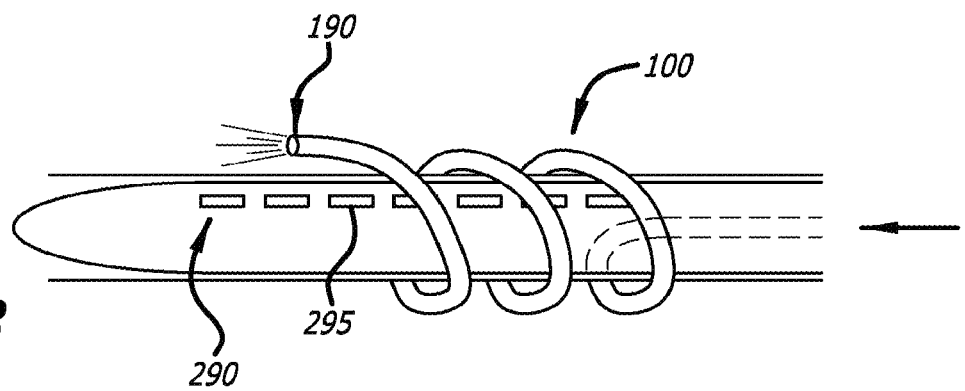
FIG. 3 illustrates the use of an embodiment in which the implant transmits light that helps determine its location within tissue.

In certain embodiments, it is preferable to know the relative locations of the urethral sphincter and bladder with respect to prostate prior to and/or during the implantation of an extra-urethral implant. Further, it may be preferable to know where the extra-urethral implant is being deployed relative to the structures. In such embodiments, the delivery device 200 can include a transurethral imaging device. Typically, imaging devices onboard a delivery device 200 can have transmitters 210 and receivers 210 near the delivery port 220, as depicted in FIG. 2. Other embodiments can provide similar location information using optics systems. For example, in certain embodiments in which the extra-urethral implant is polymeric, the polymeric material can be chosen such that it is capable of transmitting light in addition to having desirable mechanical properties. FIG. 3 depicts the distal end 190 of the implant functions as a beacon, and can be detected by optical sensors 295 on board the delivery device. In one example, the multiple sensors 295 can track the position of the distal end 190 of the implant even though the implant is within the extra-urethral region by detecting the light emitted from the distal end 190 of the implant. By moving the distal end 290 of the delivery device, which allows multiple sensors 295 to collect light, the precise position of the implant can be determined. This kind of precise tracking and positioning can help avoid damaging sensitive parts of the local anatomy.

Figure 4A:
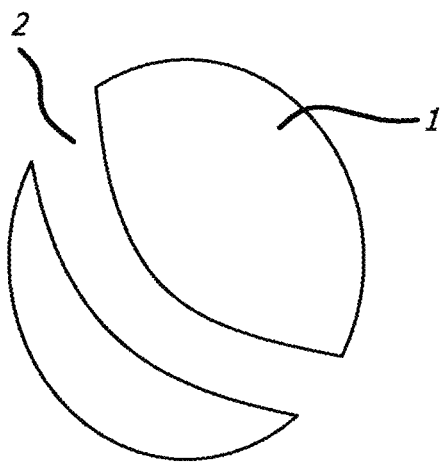
FIGS. 4A through 4E illustrate views of the challenges of implanting a device that straightens a naturally bent urethra.
Figure 4B:
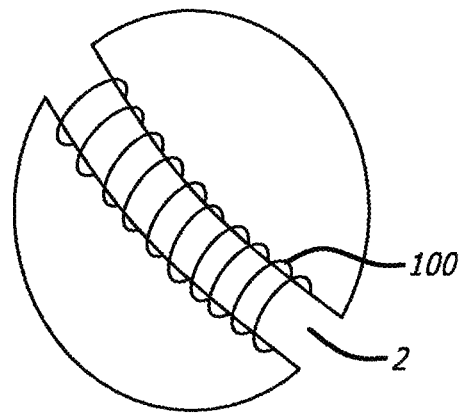
Figure 4C:
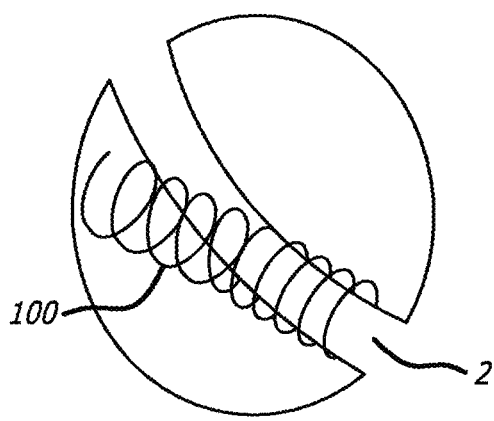
Figure 4D:
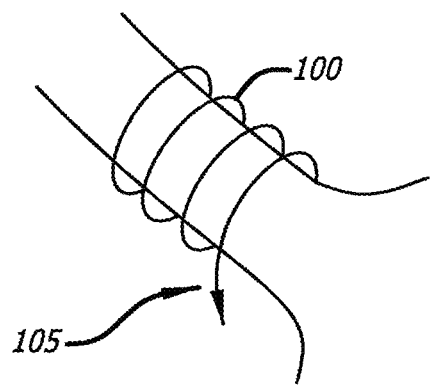
Figure 4E:
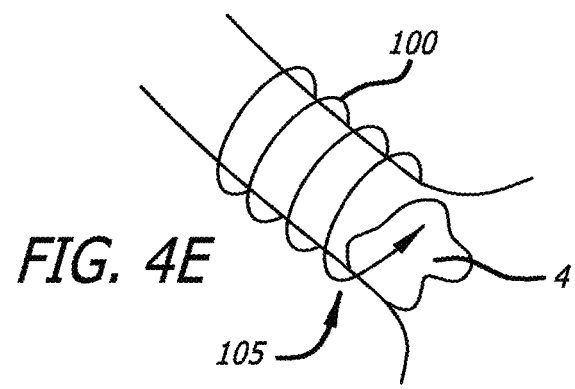

FIGS. 4A through 4E illustrate the challenges of providing a mechanically-resilient implant in the prostatic urethra. FIG. 4A depicts a view of a bend in the urethra 2. Because the implant is driven into and/or through tissue, the implant should have a sufficient degree of stiffness and strength. FIG. 4B depicts implant 100 within the extra-urethral region after having been driven through tissue. FIG. 4B depicts the urethra 2 as now straightened as compared to its previously bent condition depicted in FIG. 4A. However, over time the mechanical resilience, strength, and stiffness of the implant can have unwanted effects, as depicted in FIG. 4C. The implant in FIG. 4C has caused distortions in the prostatic tissue that in turn later caused migration of the implant 100 through tissue. Further, FIGS. 4D and 4E depict the sharp tip 105 of an implant 100 that migrates or cuts through tissue leading to erosion of tissue 4 and exposure of the implant to urine. As discussed above, chronic exposure to urine can lead to encrustation and further complications.

To accommodate this balance between the strength and stiffness needed to penetrate tissue and the flexibility and conformability needed to avoid damaging tissue in a chronic implant environment, it is preferable in certain embodiments to use a two-stage implantation process. In such a two-stage implantation, a stiff, sharp tool is advanced into tissue. Next a softer and/or less stiff implant is left behind when the delivery tool is retracted. In embodiments in which the first stage of implantation is accomplished by delivering energy to tissue, the implant can remain outside the area where energy is being delivered until implantation. In this way, the implant does not experience the delivery energy, which can be advantageous if the delivery energy would have an adverse effect on the implant.

Figure 5:
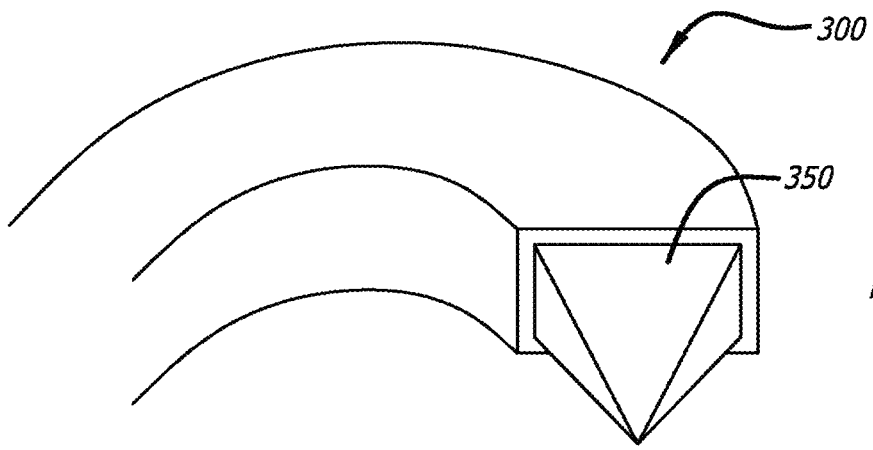
FIG. 5 illustrates a view of a delivery tool and implant in which the implant rides on the outside of the delivery tool according to an embodiment. The delivery tool is stiff and sharp as compared to the implant.

FIG. 5 illustrates a stiff delivery tool 350 and a comparatively less stiff implant 300 to be left behind when the delivery tool 350 is retracted. The core is stiff and sharp, which is preferable for driving into tissue to enable delivery of the more supple sheath implant 300 around the sharp core. Upon retraction, the comparatively less stiff sheath implant 300 is left behind as the extra-urethral implant. Preferably, the sheath has column strength substantial enough such that it does not peel back from the core when the core is being driven through tissue.

Figure 6:
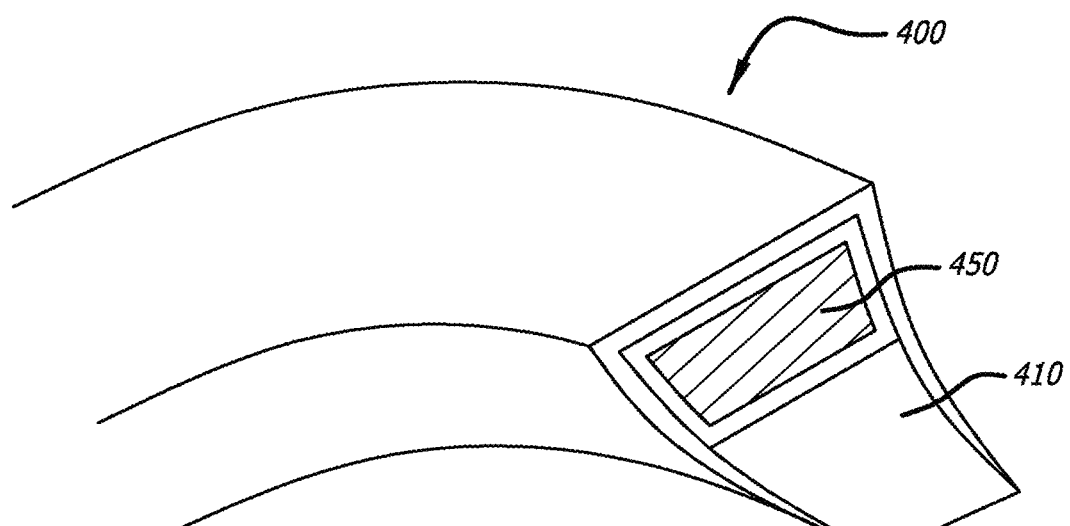
FIG. 6 illustrates a view of a delivery tool and implant in which the implant is contained within the delivery tool according to an embodiment. The delivery tool is stiff and sharp as compared to the implant.

FIG. 6 illustrates another embodiment of a stiff delivery tool 400 and a comparatively less stiff implant 450 to be left behind when to delivery tool 400 is retracted. In this embodiment, the delivery tool 400 is external to the implant 450. The external delivery tool 400 is depicted as having a rectangular cross-section, but other cross-sections that facilitate directed delivery of the extra-urethral implant can also be used. The tip 410 of the delivery tool should be non-coring such that material does not build up at the tip of the delivery tool 400 and retard the progress of the delivery tool 400 and implant 450 through tissue. Advantageously, in this embodiment the implant 450 can have less column strength than the embodiment of FIG. 5 in which the implant is external to the delivery tool because the implant 450 in the embodiment of FIG. 6 is comparatively protected within the delivery tool 400. Further, the implant surface does not pass through tissue during delivery and so the implant 450 sees none of the frictional forces that the implant of the embodiment of FIG. 5 sees since it is external to the delivery tool.

FIGS. 7A through 7C depict the delivery process of embodiments in which both the implant core 450 and the delivery tool 400 are advanced through tissue in the deployment phase. FIG. 7A depicts a helical shape for the distal end 420 of delivery tool 400. Implant core 450 is within this distal end 420 of delivery tool 400. FIG. 7A depicts lock mechanisms 480 at a region proximal to the implant core 450. These lock mechanisms 480 allow the delivery tool 400 and the implant core 450 to be manipulated together or separately by selectively locking or unlocking the delivery tool 400 and the implant core 450 with respect to each other. FIG. 7B depicts delivery school 400 being retracted while the implant pusher 488 is held fixed by some of the locking mechanisms 480. In this way, the internal implant core 450 is extruded into tissue. FIG. 7C further depicts a sectional view to illustrate the implant pusher 488 enabling delivery of the implant 450. The pusher 488 must be long enough to exit the urethra such that the implant 450 is fully embedded away from the urethral lumen, that is, the implant 450 is delivered to an extra-urethral position.

Figure 8A:
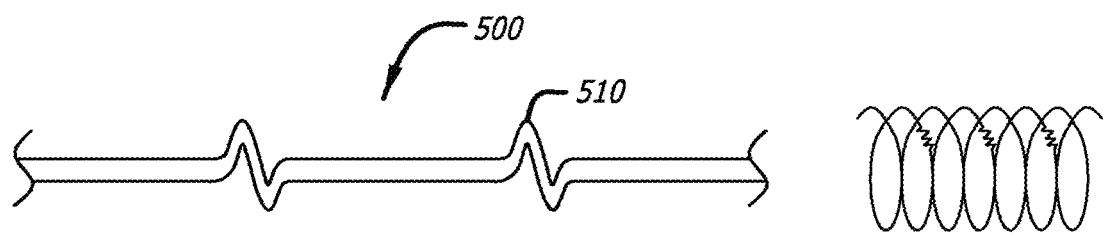
FIGS. 8A through 8C illustrate views of an embodiment of an implant with longitudinal flexibility to accommodate urethral anatomy.
Figure 8B:
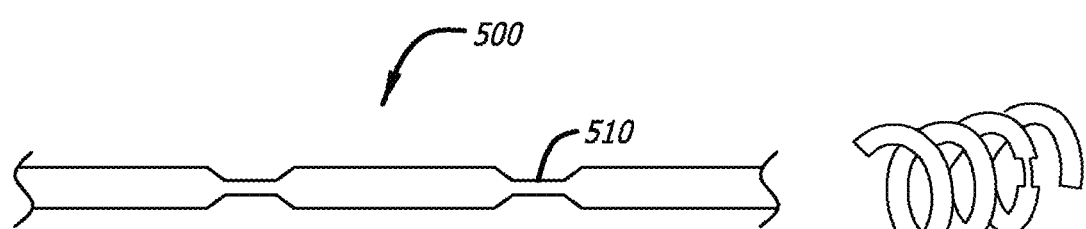
Figure 8C:
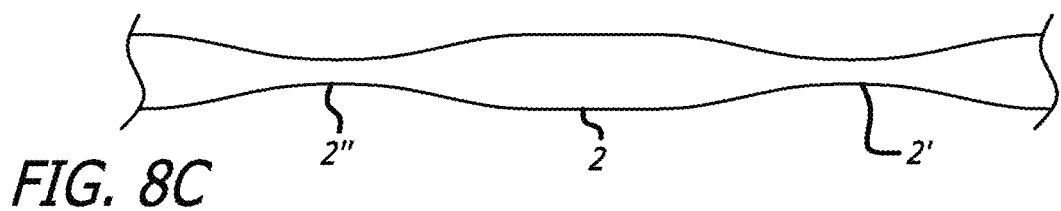

FIGS. 8A through 8C depict embodiments that can accommodate the variations of urethral anatomy while still providing the desired mechanical properties to enlarge the urethral lumen. Extra-urethral implants may need to flex longitudinally to avoid straightening the natural geometry of the urethra. Such straightening could cause discomfort and may lead to migration of the implant within tissue. FIGS. 8A and 8B depict two configurations of an embodiment of a variable strength extra-urethral implant and FIG. 8C depicts the prostatic urethra after implantation of such variable strength extra-urethral implants. As depicted in FIGS. 8A and 8B, an extra-urethral implant can have variable strength segments. Some flexible segments 510 can have hinge-like geometries to relieve longitudinal stress. The extra-urethral implant 500 can act similar to a series of independent rings rather than a straight coil. FIG. 8C depicts wider segments 2' of the urethra 2 in which the stiffer segments of the extra-urethral implant 500 have enlarged the urethral lumen and narrower segments 2" in which the flexible segments 510 have exerted less mechanical before action on the urethra 2. Although the entire length of the prostatic urethra has not been enlarged, it is believed that small narrowed segments coupled with a majority of large segments can still reduce or relieve symptoms of BPH.

Figure 9:
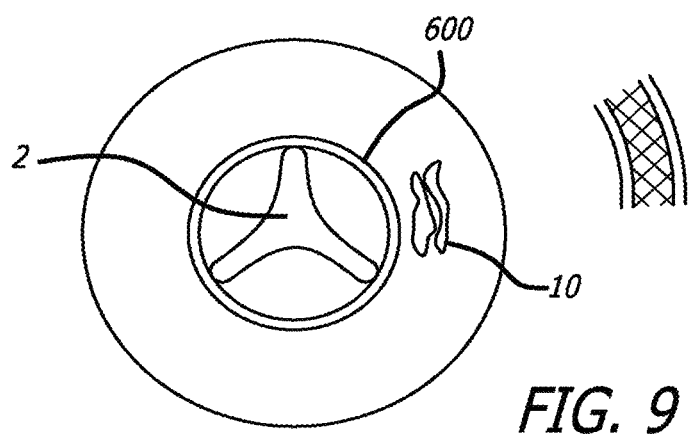
FIG. 9 depicts an embodiment in which the impingement of further hyperplasia on the urethral lumen is limited.

FIG. 9 depicts a benefit of extra-urethral implants 600 that substantially encircle the urethral lumen 2. The benefit of encircling the urethral lumen is that hyperplasia subsequent to implantation of the extra-urethral implant 600 can be physically prevented from impinging on the urethral lumen. The extra-urethral implant 600 provides a physical barrier from further cell growth that narrows the urethral lumen.

Figure 10A:
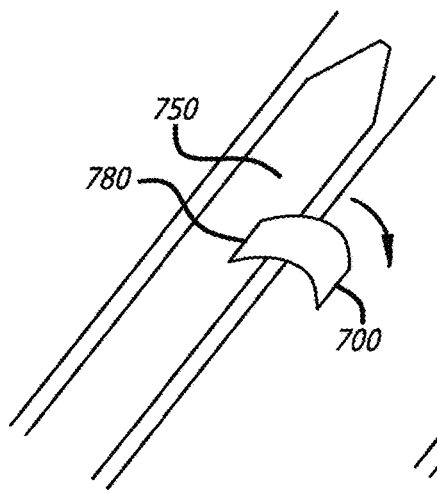
FIGS. 10A through 10C illustrate views of an embodiment in which an implant is placed that provides radial force without significant longitudinal displacement.
Figure 10B:
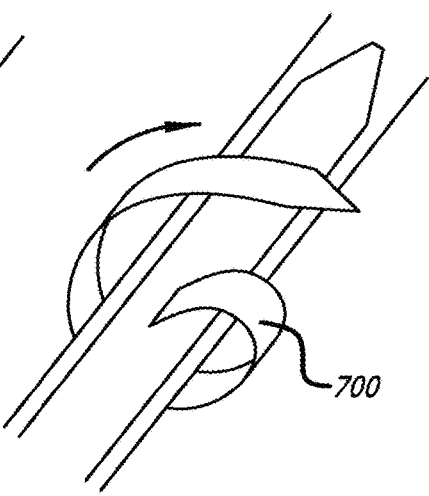
Figure 10C:
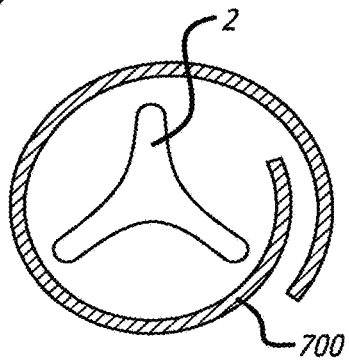

In some embodiments, controlling the extra-urethral implant as it advances longitudinally can be challenging in that it is preferable to keep the implant roughly coaxial with the lumen of the urethra. However, the urethra does not always have a straight geometry. In certain embodiments, the implant can be radially expanding, but without translating significantly along the longitudinal axis of the urethra. FIGS. 10A through 10C depicts an embodiment in which the extra-urethral implant is capable of radial expansion sufficient to displace urethral tissue, but without significant translation along the longitudinal axis of the urethra. FIG. 10A depicts delivery tool 750 within the urethral lumen and extra-urethral implant 700 advancing out of delivery port 780. Extra-urethral implant 700 has a sharp tip which enables it to advance through tissue. Extra-urethral implant 700 is sized and configured such that it provides outwardly radial force to mechanically enlarge the urethral lumen without generating significant longitudinal forces. That is, extra-urethral implant 700 is sized and configured to sufficiently circumscribe, or at least partially circumscribe, the urethral lumen. Multiple extra-urethral implants 700 can be delivered using delivery tool 752 the same prostatic urethra. Delivering multiple extra-urethral implant 700 provides enlargement of the urethral lumen along a length of the prostatic urethra. Such multiple extra-urethral implants 700 also have the benefit of avoiding the straightening problems described above.

Figure 11A:
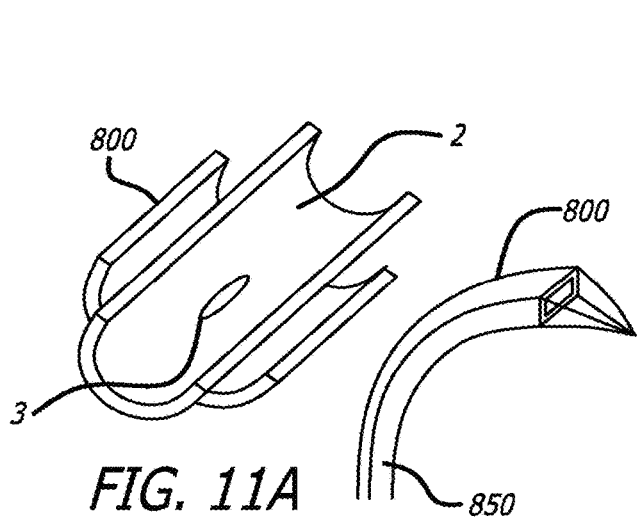
FIGS. 11A through 11C illustrate views of an embodiment in which the implant expands after being placed by a delivery tool. The implant is carried within the delivery tool.
Figure 11B:
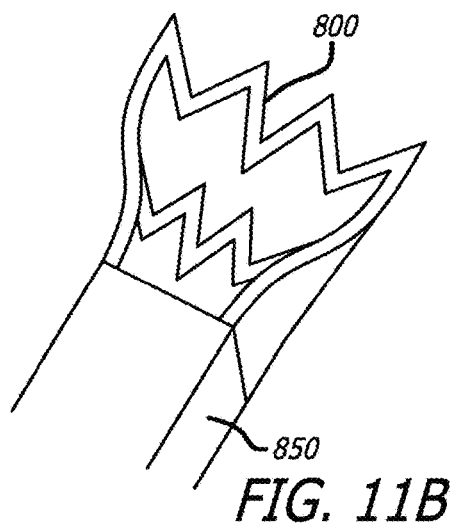
Figure 11C:
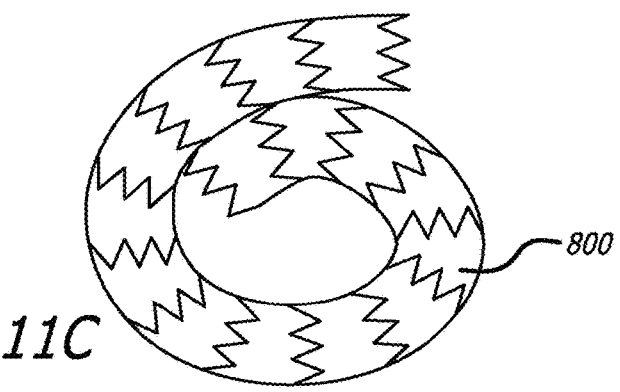

FIGS. 11A through 11C illustrate yet another embodiment of an extra-urethral implant 800. In this embodiment, the deployment of the extra-urethral implant 800 can be in two stages. First, deployment tool 850 cuts a deployment path for the implant. Then, the implant 800 is deployed and, within the peri-urethral region, expands to a larger diameter than the deployment tool 850. FIG. 11A depicts a cross-section of the prostatic urethra 2 with entry hole 3. Extra-urethral implant 800 resides in the peri-urethral space. FIG. 11A also depicts a view of the constrained configuration of implant 800 within deployment tool 850. In FIG. 11B, extra-urethral implant 800 is shown advancing relative to the end of the deployment tool 850 and simultaneously expanding to an expanded configuration. As disclosed in other embodiments herein, extra-urethral implant 800 can be advanced relative to deployment tool 850 by various mechanisms, including but not limited to, a pusher. FIG. 11C depicts extra-urethral implant 800 in an expanded and delivered configuration. In this configuration, extra-urethral implant 800 is shown as having overlapping ends but the implant need only circumscribe enough of the prostatic urethra to create the desired mechanical enlargement of the urethral lumen.

Figure 12A:
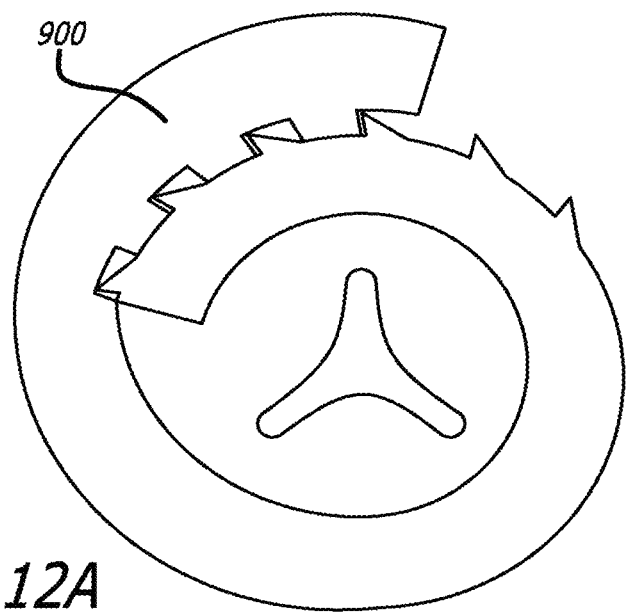
FIGS. 12A through 12B illustrate views of an implant that is frictionally connected to itself and deployed using a dilating member according to an embodiment.
Figure 12B:
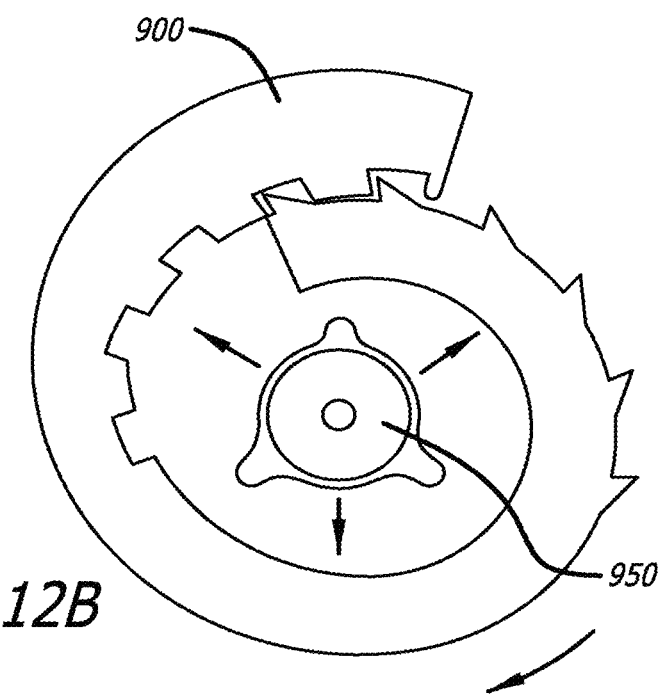

FIGS. 12A and 12B depict another embodiment of an extra-urethral implant 900. In this embodiment, the implant is frictionally connected with itself such that after initial deployment, or at a later stage, the implant could be expanded through dilation of urethra and ratcheting of the frictionally connected surfaces. FIGS. 12A and 12B depict a ring having an at least partially external loop that is in interlocking contact with an at least partially internal loop. A dilation member 950, such as a balloon, within the urethra is used to force peri-urethral tissue outward. These outward forces cause the implant to ratchet to a larger diameter. The implant will then hold peri-urethral tissue further way radially from the lumen of the urethra. This implant can be implanted initially using any of the delivery and deployment methods described herein.

Figure 13:
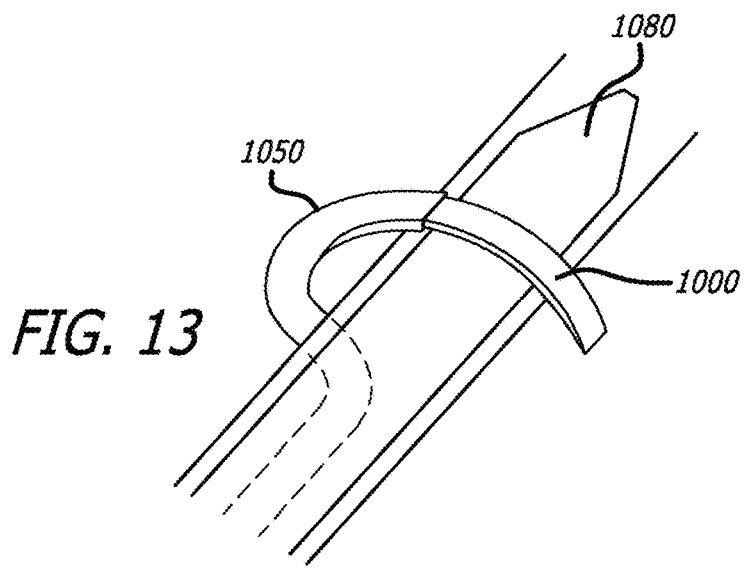
FIG. 13 illustrates views of an embodiment in which the delivery tool has a tighter radius than the implant.

One of the challenges of expanding a narrowed urethral lumen with a coil or ring-like device is that the lumen initially has a smaller diameter and tighter radius of curvature than it will have after treatment. Some of the embodiments described herein address that challenge by expanding after deployment. FIG. 13 illustrates an embodiment in which the radius of cutting tool 1050 is tighter than the radius of extra-urethral implant 1000. Cutting tool 1050 is deployed from delivery tool 1080 and cuts into the peri-urethral space to provided deployment path for extra-urethral implant 1000. Cutting tool 1050 sets the initial deployment trajectory of the extra-urethral implant 1000, but after delivery by advancing with respect to the cutting tool 1050 the extra-urethral implant 1000 can assume greater diameter and corresponding lesser radius of curvature.

Figure 14A:
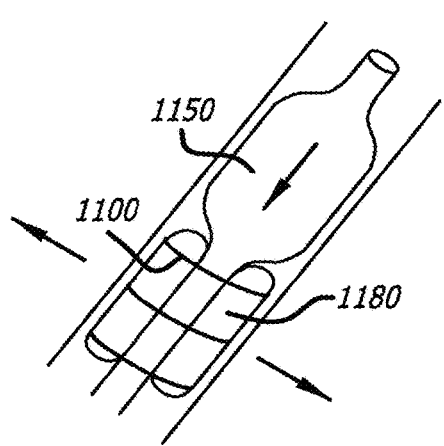
FIGS. 14A through 14C illustrative views of an embodiment in which the urethral lumen is enlarged prior to delivery of the implant.
Figure 14B:
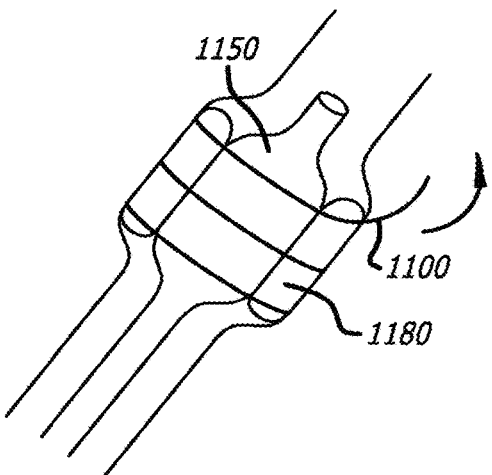
Figure 14C:
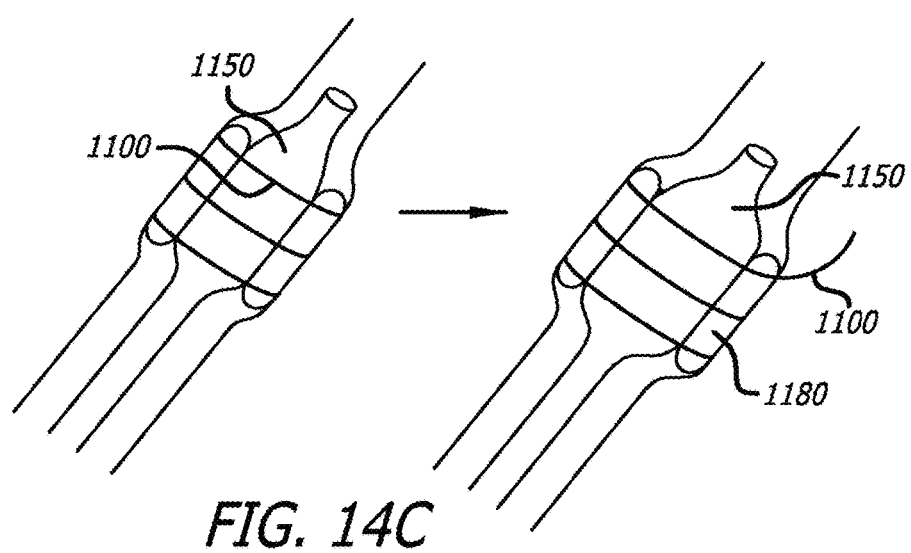

In yet another embodiment depicted in FIGS. 14A through 14C, a delivery system 1150 can be expanded at the delivery site such that the coil diameter starts deployment at the maximal urethral diameter. That is, rather than using the extra-urethral implant 1100 to expand the urethral diameter, the expansion device 1150 is used to expand the urethral diameter and the extra-urethral implant 1100 is used to maintain such expanded diameter. By expanding the deployment site, the extra-urethral implant 1100 has less diameter change post deployment. Reduced diameter change post deployment can allow for a higher degree of control over the coil trajectory. FIG. 14A shows the delivery system expanded distal to the deployment site and then moved proximally to force the distal end of extra-urethral implant 1100 into the urethral wall before the rest of the implant. By rotating the implant 1100 using members of 1180 while simultaneously pulling delivery system 1150 approximately and/or further expanding delivery system 1150, extra-urethral implant 1100 can be deployed into the peri-urethral space, as depicted in FIGS. 14B and 14C.

In yet another embodiment depicted in FIGS. 15A through 15C, the delivery of the extra-urethral implant 1100 could be from the bladder into the prostatic urethra. In this embodiment, the very large space of the bladder can be used advantageously to position and deliver the extra-urethral implant. The delivery process is similar to that depicted in the embodiment of FIGS. 14A through 14C. In both of these embodiments, a combination of expansion, translation, and direction of rotation works to deliver the extra-urethral implant at the desired location and diameter. Further, access could be suprapubic and into the bladder as depicted in FIG. 16. Such a delivery route can give the operator more control for delivery in the ability to avoid expanding the delivery system in situ.

Figure 17A:
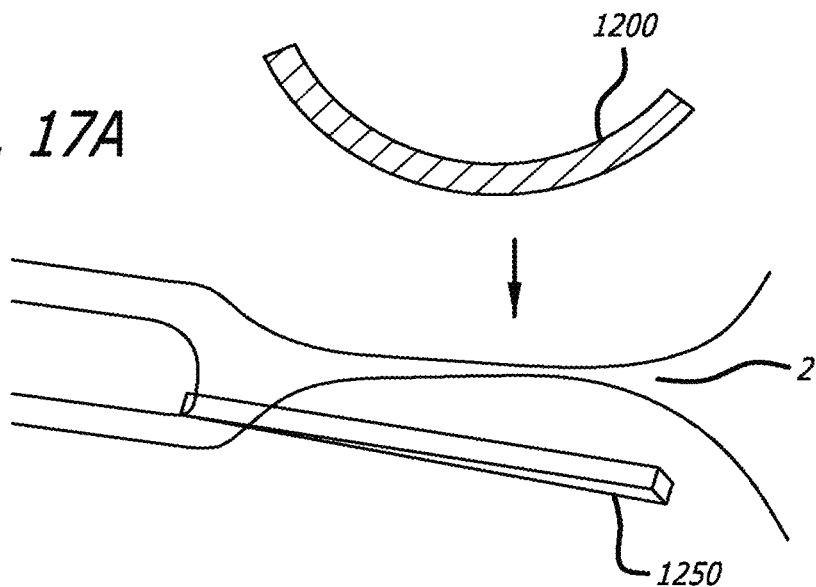
FIGS. 17A through 17C illustrative views of an arcuate implant and its delivery method according to an embodiment.
Figure 17B:
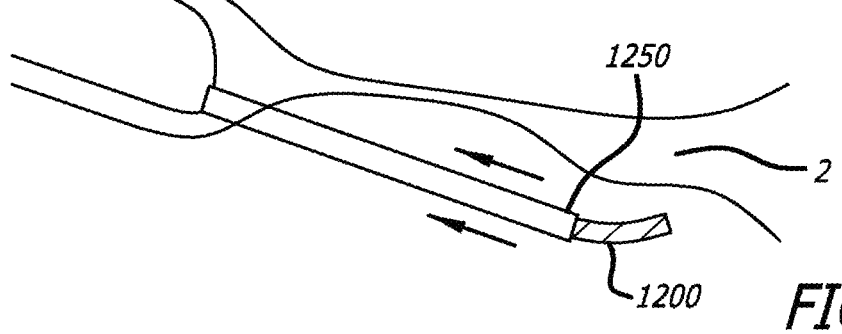
Figure 17C:
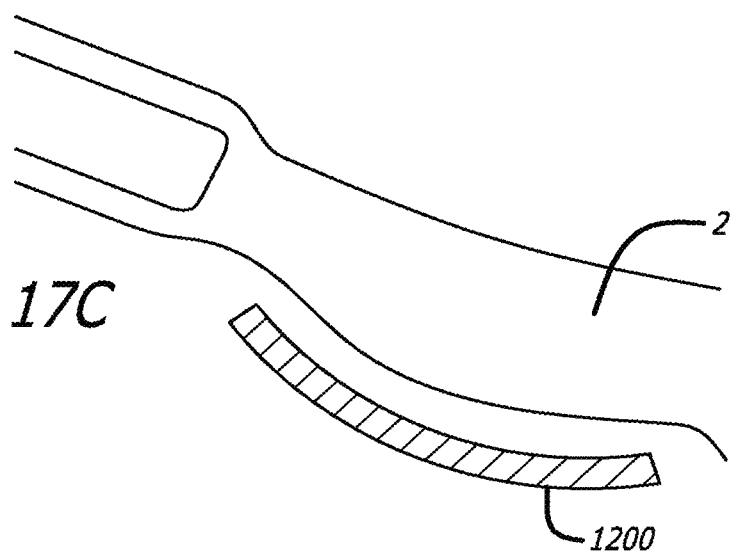

FIGS. 17A through 17C illustrate an arcuate extra-urethral implant 1200 being positioned in the peri-urethral space to enlarge the urethral lumen. The extra-urethral implant 1200 is carried within deployment tool 1250. As with other embodiments described herein, the deployment tool 1250 cuts into the peri-urethral space and the implant 1200 is advanced with respect to the deployment tool 1250. While within the deployment tool 1250, the extra urethral implant 1200 is in a substantially straight configuration. Upon deployment the extra-urethral implant 1200 can assume an arcuate configuration that helps enlarge the urethral lumen. As with other embodiments described herein, multiple implants can be positioned along the length of the prostatic urethra to achieve the desired level of enlargement.

Recalling the balance between the strength and stiffness needed to penetrate tissue and the flexibility and conformability needed to avoid damaging tissue in a chronic implant environment, other two-stage processes can be used. For example, in some subjects the tissue in the peri-urethral space can be made more mechanically resilient by a denaturing process. That is, the tissue in the peri-urethral space can be exposed to conditions that will "toughen" the tissue. Such conditions include, but are not limited to, exposure to radiofrequency heating, chemical agents, biological agents, laser energy, microwave energy, low temperatures, or equivalent means of altering the mechanical properties of tissue to cross-link portions of the tissue or otherwise stiffen the tissue. In these embodiments, the first stage can include exposure to such conditions prior to, during, or after a cutting/penetration step. Alternatively, the tissue-toughening conditions can be the first stage, and the second stage can be implantation of a self-cutting extra-urethral implant. This two-stage tissue denaturing, toughening, and/or stiffening process can be used with any of the embodiments disclosed herein or their equivalents.

Referring again to the balance between strength and stiffness needed to penetrate tissue and the flexibility and conformability needed to avoid damaging tissue in a chronic implant environment, the surface of an extra-urethral implant can be configured to enhance the mechanical coupling between the peri-urethral tissue and the implant. The peri-urethral space may contain predominantly glandular tissue that has low mechanical resilience. That is, the glandular tissue is significantly less stiff than the implant. This large mismatch in mechanical properties can be reduced by configuring the surface of the extra-urethral implant. Texture or surface features can increase the surface area contact between the implant and the prostatic tissue. Increased contact area increases the strength of the contact between the implant and the prostatic tissue. Thus, this embodiment helps overcome the mechanical mismatch between the soft, spongy prostatic tissue and the extra-urethral implant.

Figure 18:
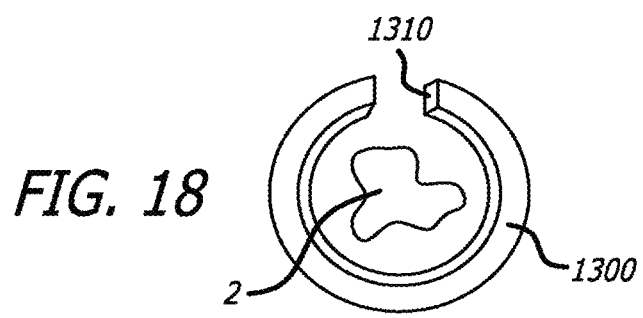
FIG. 18 illustrates a view of a self-cutting ring-type implant according to an embodiment.

FIG. 18 depicts another embodiment of an extra-urethral implant 1300, which may be implanted by inserting the implant 1300 around a lumen, moving it circumferentially around the lumen using a sharp leading edge 1310 to penetrate tissue.

Figure 19:
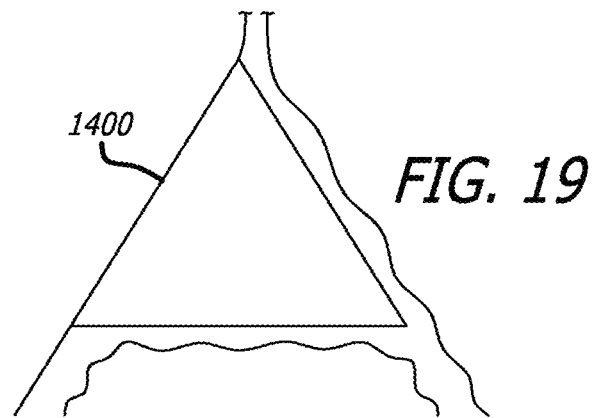
FIG. 19 illustrates a view of a triangular implant according to an embodiment.

In the embodiment depicted in FIG. 19 a circumferential implant is modeled after the shape of an obstructed urethra, for instance in a triangular shape, and inserted into extra-urethral tissue. This non-circular shape can address the challenge of displacing prostatic tissue in an anatomically-tolerable way to limit migration and provide long-term implant positional stability.

Figure 20:
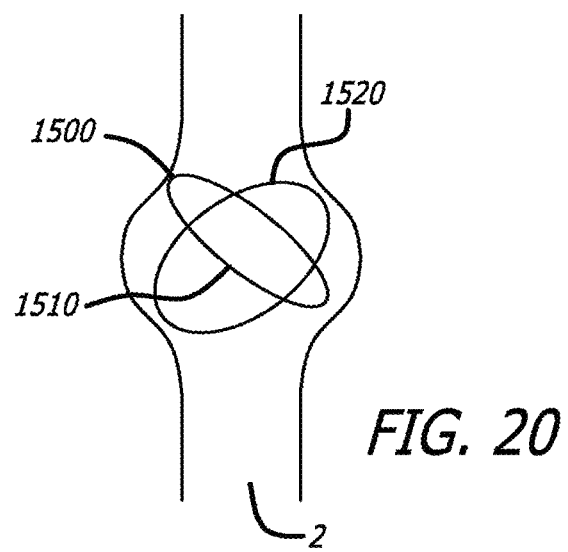
FIG. 20 illustrates a view of an implant consisting of nested rings according to an embodiment.

In the embodiment depicted in FIG. 20, a pair of nested rings, 1510 and 1520, forms the implant 1500. The rings may be introduced in a co-planar configuration and then spread apart to widen a body lumen.

Figure 21:
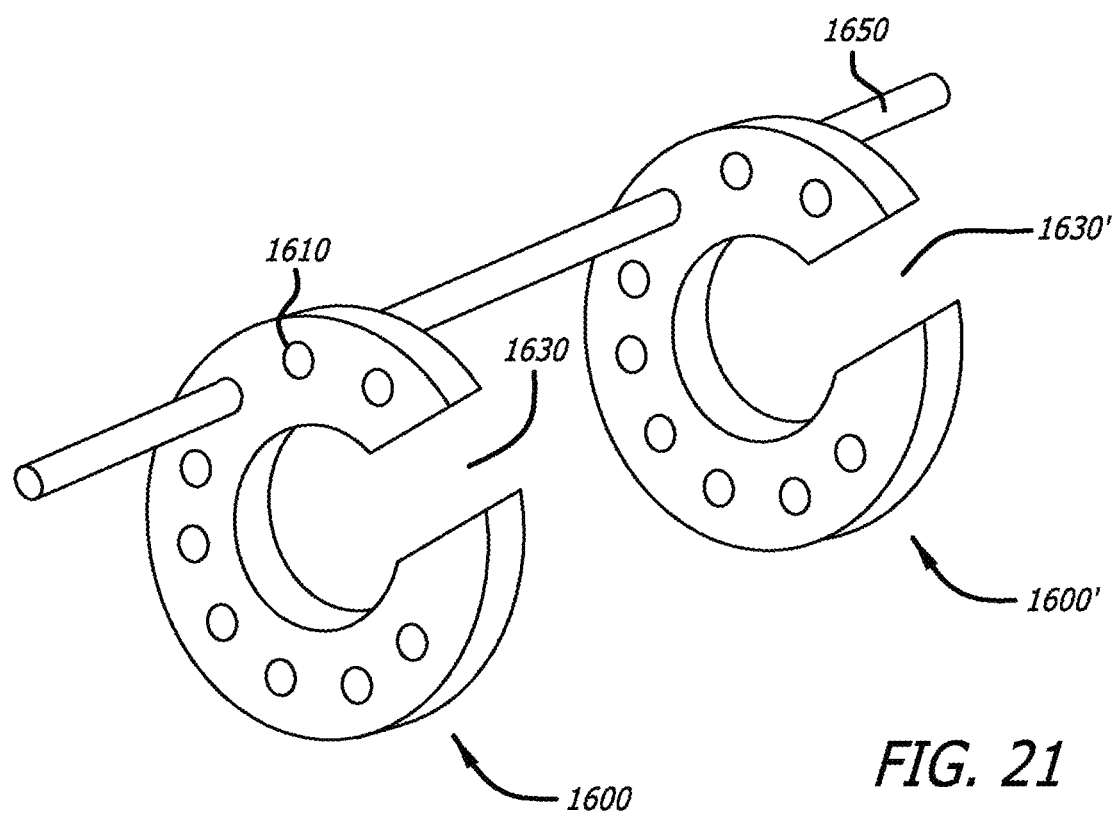
FIG. 21 illustrates a view of a series of implants connected by a flexible spine according to an embodiment.

Certain embodiments of the invention include a ring that at least partially circumscribes the urethral lumen. Effective treatment of a length of prostatic urethra may require placement of multiple rings. When multiple rings are placed, one or more of the rings may shift over time and no longer provide effective opening of the urethral lumen. FIG. 21 depicts a series of rings (1600, 1600') connected by comparatively flexible spine 1650. The spine 1650 can help prevent the rings from shifting, twisting, or otherwise moving out of position. In certain embodiments, the spine 1650 can be attached to the rings 1600, 1600' after placement of one or more of the rings. In other embodiments, the spine is connected to the rings prior to placement of the rings. FIG. 21 depicts several holes 1610 which aid in connection the spine 1650 to the rings. FIG. 21 also depicts each ring 1600, 1600' as having slot openings 1630, 1630', which aid the placement of the rings about the prostatic urethra as described in embodiments disclosed herein. Slot openings 1630 and 1630' do not have to be rotationally aligned as they are depicted in the FIG. 21 and may preferable be purposely misaligned to prevent a longitudinal segment of the prostatic urethra from being unsupported.

Certain embodiments of the invention include V-shaped extra-urethral implants. The implants are positioned such that the vertex of the V is placed outside the prostatic capsule and the legs of the V penetrate through urethral tissue and terminate in the peri-urethral space. Since the vertex is placed outside the comparatively stiffer prostatic capsule, the vertex is anchored more than it would be if it was placed within the softer tissue of the prostate gland. With the vertex placed and the prostatic capsule acting like a fulcrum, the legs of the V spread to open the angle of the V and enlarge the portion of the prostatic urethra adjacent the legs of the V. The legs can be inelastically deformed when spread by a delivery tool, such as an expanding member. Or, the legs may be compressed together during implantation and then spread when released by a delivery tool.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art.

What is claimed is:

1. A system for implantation in a lumen of a urethra, comprising:
    a delivery device configured to carry and deliver an implant;
    an implant comprising two rings connected by a single flexible spine oriented in a longitudinal direction of the urethra, each of the rings having a non-circular cross-sectional shape such that the cross-sectional shape substantially conforms to the cross-sectional shape of the urethra; and
    a pusher mechanism and lock mechanism on the delivery device connecting a distal end portion of the delivery device and a proximal end portion of the implant, wherein the lock mechanism comprises at least two opposing surfaces configured to hold a longitudinally oriented portion of the implant between the surfaces.

2. The system of claim 1 wherein the non-circular cross-sectional shape of each of the rings is a triangular shape.

3. The system of claim 1 wherein the implant is configured to have a first configuration to a second configuration.

4. The system of claim 3 wherein the first configuration is a constrained configuration and the second configuration is an expanded configuration.

5. The system of claim 4 wherein the implant is configured to provide an outward radial force on the urethra in the expanded configuration.

6. The system of claim 3 wherein the implant self-expands from the first configuration to the second configuration.

7. The system of claim 3 wherein the delivery device causes the implant to change from the first configuration to the second configuration.

8. The system of claim 3 wherein the implant is configured to provide an outward radial force on the urethra in the second configuration.

9. The system of claim 1 wherein the implant is configured to provide an outward radial force on the urethra.

10. The implant of claim 1 wherein the non-circular cross-sectional shape of each of the rings is a semi-circular shape.

11. An implant for treating a urethral lumen, comprising two rings connected by a single flexible spine oriented in a longitudinal direction of the urethra, each of the rings having a plurality of legs arranged in triangular shape, wherein the implant has a delivery configuration and a deployed configuration and is connected to a delivery device via a pushing mechanism and an locking mechanism on the delivery device, the locking mechanism comprising at least two opposing surfaces configured to hold a longitudinally oriented portion of the implant between the surfaces.

12. The implant of claim 11 wherein the delivery configuration has a smaller cross-section than the deployed configuration.

13. The implant of claim 11 wherein the implant self-expands from the delivery configuration to the deployed configuration.

14. The implant of claim 11 wherein the implant is expanded from the delivery configuration to the deployed configuration using a delivery tool.

15. The implant of claim 11 wherein the implant is configured to provide an outward radial force on the urethra.

16. The implant of claim 11 wherein the implant is configured to provide an outward radial force on the urethra in the deployed configuration.

* * * * *